United States Patent
Glover

(10) Patent No.: US 11,142,788 B2
(45) Date of Patent: *Oct. 12, 2021

(54) ISOLATION OF TARGET NUCLEIC ACIDS

(71) Applicant: GENETICS RESEARCH, LLC, Wakefield, MA (US)

(72) Inventor: William Glover, Wakefield, MA (US)

(73) Assignee: GENETICS RESEARCH, LLC, Worcester, MA (US)

( * ) Notice: Subject to any disclaimer, the term of this patent is extended or adjusted under 35 U.S.C. 154(b) by 237 days.

This patent is subject to a terminal disclaimer.

(21) Appl. No.: 16/007,514

(22) Filed: Jun. 13, 2018

(65) Prior Publication Data
US 2018/0355419 A1 Dec. 13, 2018

Related U.S. Application Data

(60) Provisional application No. 62/526,091, filed on Jun. 28, 2017, provisional application No. 62/519,051, filed on Jun. 13, 2017.

(51) Int. Cl.
- C12Q 1/68 (2018.01)
- C12Q 1/6853 (2018.01)
- C12Q 1/6844 (2018.01)
- C12Q 1/6827 (2018.01)
- C12Q 1/682 (2018.01)
- C12Q 1/6811 (2018.01)
- C12Q 1/6876 (2018.01)
- C12Q 1/6806 (2018.01)

(52) U.S. Cl.
CPC .......... *C12Q 1/6853* (2013.01); *C12Q 1/682* (2013.01); *C12Q 1/6806* (2013.01); *C12Q 1/6811* (2013.01); *C12Q 1/6827* (2013.01); *C12Q 1/6846* (2013.01); *C12Q 1/6876* (2013.01); *C12N 2310/333* (2013.01); *C12N 2310/334* (2013.01); *C12N 2310/335* (2013.01); *C12Q 2521/319* (2013.01)

(58) Field of Classification Search
None
See application file for complete search history.

(56) References Cited

U.S. PATENT DOCUMENTS

| | | | |
|---|---|---|---|
| 6,297,010 B1 | 10/2001 | Stefano | |
| 6,610,486 B1* | 8/2003 | Dahlhauser | C12Q 1/6827 435/194 |
| 8,318,445 B2 | 11/2012 | Bernard et al. | |
| 10,011,849 B1 | 7/2018 | Gill et al. | |
| 10,081,829 B1 | 9/2018 | Shuber et al. | |
| 2003/0215854 A1 | 11/2003 | Clausen et al. | |
| 2004/0197804 A1 | 10/2004 | Keefe et al. | |
| 2006/0183109 A1 | 8/2006 | Dahlberg et al. | |
| 2008/0254516 A1 | 10/2008 | St. John et al. | |
| 2009/0053715 A1 | 2/2009 | Dahlhauser | |
| 2012/0315633 A1 | 12/2012 | Mantzaris et al. | |
| 2013/0059762 A1 | 3/2013 | Leamon et al. | |
| 2014/0356867 A1 | 12/2014 | Peter et al. | |
| 2015/0105284 A1 | 4/2015 | Willson et al. | |
| 2015/0211058 A1* | 7/2015 | Carstens | C12Q 1/6844 435/5 |
| 2015/0292033 A1 | 10/2015 | Wang et al. | |
| 2016/0002720 A1 | 1/2016 | Richard | |
| 2016/0017396 A1 | 1/2016 | Cann et al. | |
| 2016/0130664 A1 | 5/2016 | Albitar | |
| 2016/0153005 A1 | 6/2016 | Zhang et al. | |
| 2016/0319262 A1 | 11/2016 | Doudna et al. | |
| 2017/0022551 A1 | 1/2017 | Liu et al. | |
| 2017/0044592 A1 | 2/2017 | Peter et al. | |
| 2017/0053062 A1 | 2/2017 | Cradick et al. | |
| 2017/0114413 A1 | 4/2017 | Hahn et al. | |

FOREIGN PATENT DOCUMENTS

| | | |
|---|---|---|
| EP | 3150718 A1 | 4/2017 |
| WO | 1995/006752 A1 | 3/1995 |
| WO | 99/39003 A1 | 8/1999 |
| WO | 2000/011222 A1 | 3/2000 |
| WO | 2003/027258 A2 | 4/2003 |
| WO | 2008/104794 A2 | 9/2008 |
| WO | 2010/014920 A1 | 2/2010 |
| WO | 2015/075056 A1 | 5/2015 |
| WO | 2016/014409 A1 | 1/2016 |

(Continued)

OTHER PUBLICATIONS

Gillar et al. (Journal of Chromatography, 1998, 714, p. 13-20) (Year: 1998).*
Zhang et al. (Analyst, 2015, 140:4030-4036) (Year: 2015).*
Of Wang et al. (Molecular Therapy—Nucleic Acids, 2016, 5:e388) (Year: 2016).*
Altmuller, 2014, Enrichment of target sequence for next-generation sequencing applications in research and diagnostics, Biol Chem 395(2)231-37.
Campesato, 2015, Comprehensive cancer-gene panels can be used to estimate mutational load and predict clinical benefit to PD-1 blockade in clinical practice, Oncotarget 6(33):34221-34227.
Chalmers, 2017, Analysis of 100,000 human cancer genomes reveals the landscape of tumor mutational burden, Genome Med 9(34):1-14.

(Continued)

*Primary Examiner* — Stephanie K Mummert
(74) *Attorney, Agent, or Firm* — Brown Rudnick LLP; Thomas C. Meyers

(57) ABSTRACT

The invention provides methods of isolating a target nucleic acid in a sample. A primer is hybridized to the target. A polymerase and modified nucleotide resistant to nuclease degradation are used to extend the primer to create a modified polynucleotide. The sample is exposed to a nuclease, thereby isolating the modified polynucleotide. Optionally, the target nucleic acid may be further protected by binding a protein in a sequence specific manner to one end of the target nucleic acid to create a protected target nucleic acid resistant to nuclease degradation. Thus, after exposing the sample to a nuclease, the modified polynucleotide and protected target nucleic acid are isolated.

21 Claims, 6 Drawing Sheets

(56) References Cited

FOREIGN PATENT DOCUMENTS

| WO | 2016/028843 A2 | 2/2016 | |
|---|---|---|---|
| WO | 2016/028887 A1 | 2/2016 | |
| WO | WO-2016028887 A1 * | 2/2016 | ............ C40B 40/06 |
| WO | 2016/094867 A1 | 6/2016 | |
| WO | 2016/100955 A2 | 6/2016 | |
| WO | 2016/100974 A1 | 6/2016 | |
| WO | 2016/134136 A2 | 8/2016 | |
| WO | 2016/144810 A1 | 9/2016 | |
| WO | 2016/172727 A1 | 10/2016 | |
| WO | 2017/031360 A1 | 2/2017 | |
| WO | 2017/053762 A1 | 3/2017 | |
| WO | 2017/218512 A1 | 12/2017 | |
| WO | 2018/068028 A1 | 4/2018 | |

OTHER PUBLICATIONS

Chen, 2018, CRISPR-Cas12a target binding unleashes indiscriminate single-stranded DNase activity, Science aar6245 (8 pages).
Deleavey, 2012, Designing chemically modified oligonucleotides for targeted gene silencing, Chem Biol 19(8):937-54.
Fu, 2013, High frequency off-target mutagenesis induced by CRISPR-Cas nucleases in human cells, Nat Biotech 31(9) 822-826.
Gootenberg, 2018, Multiplexed and portable nucleic acid detection platform with Cas13, Cas12a, and Csm6, Science aaq0179 (10 pages).
Hahn, 2009, Microsystem for isolation of fetal DNA from maternal plasma by preparative size separation, Clin Chem 55 (12):2144-2152.
Harrington, 2017, A thermostable Cas9 with increased lifetime in human plasma, Nat Commun 8(1):1424.
Hsieh, 2010, Electrochemical DNA detection via exonuclease and target-catalyzed transformation of surface-bound probes, Langmuir 26(12):10392-10396.
Hsu, 2013, DNA targeting specificity of RNA-guided Cas9 nucleases, Nat Biotech 31(9):827-832.
International Search Report and written Opinion dated Aug. 27, 2018, for PCT/US2018/037294, filed Jun. 13, 2018 (10 pages).
International Search Report and written Opinion dated Aug. 27, 2018, for PCT/US2018/037312, filed Jun. 13, 2018 (10 pages).
International Search Report and written Opinion dated Aug. 28, 2018, for PCT/US2018/037273, filed Jun. 13, 2018 (10 pages).
International Search Report and written Opinion dated Aug. 29, 2018, for PCT/US2018/037287, filed Jun. 13, 2018 (10 pages).
International Search Report and written Opinion dated Sep. 11, 2018, for PCT/US2018/037310, filed Jun. 13, 2018 (8 pages).
nternational Search Report and written Opinion dated Sep. 12, 2018, for PCT/US2018/037307, filed Jun. 13, 2018 (8 pages).
International Search Report and written Opinion dated Sep. 13, 2018, for PCT/US2018/037296, filed Jun. 13, 2018 (11 pages).
International Search Report and written Opinion dated Sep. 17, 2018, for PCT/US2018/037277, filed Jun. 13, 2018 (9 pages).
International Search Report and written Opinion dated Sep. 21, 2018, for PCT/US2018/039518, filed Jun. 26, 2018 (8 pages).
International Search Report and written Opinion dated Sep. 26, 2018, for PCT/US2018/037280, filed Jun. 13, 2018 (18 pages).
Jiang, 2015, Cas9-assisted targeting of chromosome segments catch enables one-step targeted cloning of large gene clusters.
Jinek, 2012, A programmable dual-RNA-guided DNA endonuclease in adaptive bacterial immunity, Science 337 (6096)816-821.
Kozarewa, 2015, Overview of Target Enrichment Strategies, Curr Protoc Mol Biol 112(7):1-23.
Larsson, 2004, In situ genotyping individual DNA molecules by target-primed rolling-circle amplification of padlock probes, Nat Meth 1(3):227-232.
Lee, 2017, CUT-PCR: CRISPR-mediated ultrasensitive detection of target DNA using PCR, Ocogene 36 (49):6823-6829.
Lescarbeau, 2017, A reanalysis of Schaefer et al does not indicate extensive CRISPR/Cas9 mediated off-target editing events, bioRxiv.
Leung, 2012, Luminescent detection of DNA-binding proteins, Nucleic Acids Res 40(3):941-55.
Mertes, 2011, Targeted enrichment of genomic DNA regions for next-generation sequencing, Brief Funct Genomics 10 (6):374-86.
Monia, 1996, Nuclease resistance and antisense activity of modified oligonucleotides targeted to Ha-ras, J Biol Chem 271(24):14533-40.
Pattanayak, 2013, High-throughput profiling of off-target DNA cleavage reveals RNA-programmed Cas9 nuclease specificity, Nat Biotech 31(9)839-843.
Schaefer, 2017, Unexpected mutations after CRISPR-Cas9 editing in vivo, Nat Meth 14(6):547-550.
Tosi, 2017, Long-adapter single-strand oligonucleotide probes for the massively multiplexed cloning of kilobase genome regions, Nat Biomed Eng 1:92.
Wang, 2014, Genetic screens in human cells using the CRISPR/Cas9 system, Science 343(6166):80-84.
Wang, 2018, CRISPR-typing PCR (ctPCR), a new Cas9-based DNA detection method, Sci Rep 8(1):14126.
Xu, 2015, An improved protocol for small RNA library construction using high definition adapters, Meth Next-Gen Seq 2:1-10.
Zehir, 2017, Mutational landscape of metastatic cancer revealed from prospective clinical sequencing of 10,000 patients, Nat Med 23(6):703-713.
Zetsche, 2015, Cpf1 is a single RNA-guided endonuclease of a class 2 CRISPR-Cas system, Cell 163(2):759-71.
Zhang, 2015, Use of genome-wide association studies for cancer research and drug repositioning, PLoS One 10(3):e0116477.
Zhang, 2018, Detection of target DNA with a novel Cas9/sgRNAs-associated reverse PCR (CARP) technique, Anal Bioanal Chem 410(12):2889-2900.
Zischewski, 2017, Detection of on-target and off-target mutations generated by CRISPR/Cas9 and other sequence-specific nucleases, Biotech Adv 35(1):95-104.

* cited by examiner

PEx product should be about 36 kb

PEx product should be about 27 kb

ISOLATION OF TARGET NUCLEIC ACIDS

CROSS-REFERENCE TO RELATED APPLICATIONS

This application claims the benefit of, and priority to, U.S. Provisional Application 62/526,091, filed Jun. 28, 2017, and U.S. Provisional Application 62/519,051, filed Jun. 13, 2017, the contents of each of which are incorporated by reference.

FIELD OF THE INVENTION

The invention relates to molecular genetics.

BACKGROUND

Cancer is a leading cause of death, killing millions of people each year. Worldwide, the number of newly diagnosed cancer cases per year is expected to rise to 23.6 million by 2030. Accurate and early diagnosis is essential to improved treatment of cancer. However, early, accurate diagnosis of cancer is difficult when detection and analysis methods, such as sequencing, are time-consuming, expensive, and lack sensitivity.

More sensitive detection methods may allow for earlier detection, or detection that occurs before the disease reaches a stage when treatment is ineffective. Recommending an effective course of treatment is challenging when the diagnostic methods fail to identify the type of cancer. Mutations specific to certain types of cancer can be present in low abundance and difficult to detect without sensitive detection methods. Further, healthcare professionals are unable to accurately monitor the progression of the disease and response to treatment if the detection methods lack sensitivity. Without sensitive detection methods, cancer will continue to kill millions of people annually.

SUMMARY

The invention provides methods that isolate a target nucleic acid, such as a mutation indicative of cancer, in a sample. Methods of the invention allow for detection of elements present at low quantities, such as mutations specific to certain cancer types, in nucleic acid samples. By isolating the mutations, the invention allows for a greater depth of sequencing coverage when sequencing the isolated regions of interest or target nucleic acids. This allows for increased sampling numbers and reduces the time and costs associated with sequencing.

The sensitivity of the invention makes methods useful for monitoring the progression of disease and determining the stage of cancer. By detecting mutations present at low quantities, cancer or related diseases can be detected at early stages when effective treatment is possible. As such, healthcare professionals may use methods of the invention for an early, accurate diagnosis. Methods of the invention may further be used to predict efficacy of treatment, as progression of the disease may be monitored after treatment. Methods of the invention are also useful for other diagnostic applications that require detection of low-abundance nucleic acids.

Certain embodiments of the invention provide methods for isolating a target nucleic acid. At least one primer may be hybridized to a target nucleic acid in a sample. The primer may be extended using a polymerase and modified nucleotides that are resistant to nuclease degradation to create a modified polynucleotide. The sample may be exposed to a nuclease, such as an exonuclease, thereby isolating the modified polynucleotides.

In other embodiments, methods of the invention provide further protection and isolation of the target nucleic acid. At least one primer may be hybridized to a first end of a target nucleic acid in a sample. The primer may be extended using a polymerase and modified nucleotides that are resistant to nuclease degradation to create a modified polynucleotide. At least one protein may be bound to a second end of the target nucleic acid in a sequence-specific manner to create protected target nucleic acid resistant to nuclease degradation. The sample may be exposed to a nuclease, such as an exonuclease, thereby isolating the modified polynucleotides and protected target nucleic acid.

In preferred embodiments, the modified nucleotides comprise modified nucleotide triphosphates. In certain embodiments, natural nucleotides may be used in combination with modified nucleotides. In certain embodiments, the modified nucleotide triphosphates comprise alpha-phosphorothioate nucleotide triphosphates, morpholino triphosphates, peptide nucleic acids, peptide nucleic acid analogs, or sugar modified nucleotide triphosphates.

As a non-limiting example, the modified nucleotide triphosphates may include 2'-Deoxycytidine-5'-O-(1-Thiotriphosphate), 2'-O-methyl modified nucleotide triphosphate, 2'-fluoro modified nucleotide, 2'-O-Methyladenosine-5'-Triphosphate, 2'-O-Methylcytidine-5'-Triphosphate, 2'-O-Methylguanosine-5'-Triphosphate, 2'-O-Methyluridine-5'-Triphosphate, 2'-O-Methylinosine-5'-Triphosphate, 2'-O-Methyl-2-aminoadenosine-5'-Triphosphate, 2'-O-Methylpseudouridine-5'-Triphosphate, 2'-O-Methyl-5-methyluridine-5'-Triphosphate, 2'-O-Methyl-N6-Methyladenosine-5'-Triphosphate, 2'-Fluoro-2'-deoxyadenosine-5'-Triphosphate, 2'-Fluoro-2'-deoxycytidine-5'-Triphosphate, 2'-Fluoro-2'-deoxyguanosine-5'-Triphosphate, 2'-Fluoro-2'-deoxyuridine-5'-Triphosphate, and 2'-Fluoro-thymidine-5'-Triphosphate.

The proteins may independently be any protein that binds a nucleic acid in a sequence-specific manner. The protein may be a programmable nuclease. For example, the protein may be a CRISPR-associated (Cas) endonuclease, zinc-finger nuclease (ZFN), transcription activator-like effector nuclease (TALEN), or RNA-guided engineered nuclease (RGEN). The protein may be a catalytically inactive form of a nuclease, such as a programmable nuclease described above. The protein may be a transcription activator-like effector (TALE). The protein may be complexed with a nucleic acid that guides the protein to an end of the segment.

Embodiments of the invention use proteins that are originally encoded by genes that are associated with clustered regularly interspaced short palindromic repeats (CRISPR) in bacterial genomes. Preferred embodiments use a CRISPR-associated (Cas) endonuclease. Preferably, the protein comprises a Cas endonuclease complexed with a guide RNA that targets the Cas endonuclease to a region of the target nucleic acid. The complexes bind to the specific sequences in the nucleic acid segment by virtue of the targeting portion of the guide RNAs. When the Cas endonuclease/guide RNA complex binds to a nucleic acid segment, the complex protects that segment from digestion by exonuclease. The Cas endonuclease may be catalytically inactive.

In certain aspects, two primers may be used for hybridization. The modified polynucleotide may be amplified. Methods of the invention may further comprise dephosphorylating the target nucleic acid using a phosphatase.

Protecting a target nucleic acid with modified nucleotides or binding proteins while promiscuously digesting unprotected nucleic acid may be described as a negative enrichment for the target. Embodiments of negative enrichment may be used for the detection of "rare events" where a specific sequence of interest makes up a very small percentage of the total quantity of starting material. Specifically, negative enrichment techniques may be used to detect specific mutations in circulating tumor DNA (ctDNA) in the plasma of cancer patients, or specific mutations of interest potentially associated with fetal DNA circulating in maternal plasma. In addition, negative enrichment analysis can be applied to purified circulating tumor cells (CTCs).

Thus the invention provides methods for the detection of clinically actionable information about a subject. Methods of the invention may be used to with tumor DNA to monitor cancer remission, or to inform immunotherapy treatment. Methods may be used with fetal DNA to detect, for example, mutations characteristic of inherited genetic disorders. Methods may be used to detect and describe mutations and/or alterations in circulating tumor DNA in a blood or plasma sample that also contains an abundance of "normal", somatic DNA, Methods may be used for directly detecting structural alterations such as translocations, inversions, copy number variations, loss of heterozygosity, or large indels. The subject DNA may include circulating tumor DNA in a patient's blood or plasma, or fetal DNA in maternal blood or plasma.

In certain aspects, the invention provides a method for detecting a structural genomic alteration. The method includes hybridizing a primer to a target nucleic acid, extending the primer using polymerase and modified nucleotides resistant to nuclease degradation to create a modified polynucleotide, digesting unprotected target nucleic acid, thereby isolating the modified polynucleotide and thus the target nucleic acid. The method may further include protecting one end of a target nucleic acid in a sample by introducing Cas endonuclease/guide RNA complexes that bind to targets that flank a boundary of a genomic alteration, digesting unprotected nucleic acid, and isolating the protected target nucleic acid. The invention may further include detection of the target nucleic acid, thereby confirming the presence of the genomic alteration. The digesting step may include exposing the unprotected nucleic acid to one or more exonucleases. Preferably, the modified nucleotides are modified triphosphate nucleotides. Preferably, the Cas endonuclease/guide RNA complexes include guide RNAs with targeting regions complementary to targets that do not appear on the same chromosome in a healthy human genome.

After digestion, the protected segment of nucleic acid may be detected or analyzed by any suitable method. For example, the segment may be detected or analyzed by DNA staining, spectrophotometry, sequencing, fluorescent probe hybridization, fluorescence resonance energy transfer, optical microscopy, electron microscopy, others, or combinations thereof. The segment may be of any suitable length. Methods of the invention are useful for isolation of long fragments of DNA, and the digesting step may include isolating the segment as an intact fragment of DNA with a length of at least five thousand bases. Short fragments may be isolated in some embodiments, e.g., fragments with about 50 to a few hundred bases in length.

The method may include providing a report describing the presence of the genomic alteration in a genome of a subject.

The nucleic acid sample may be from any source of nucleic acid. The sample may be a liquid or body fluid from a subject, such as urine, blood, plasma, serum, sweat, saliva, semen, feces, or phlegm. In preferred embodiments, the sample is a blood sample, serum sample, plasma sample, urine sample, saliva sample, semen sample, feces sample, phlegm sample, or liquid biopsy.

The nucleic acid may be any naturally-occurring or artificial nucleic acid. The nucleic acid may be DNA, RNA, hybrid DNA/RNA, peptide nucleic acid (PNA), morpholine and locked nucleic acid (LNA), glycol nucleic acid (GNA), threose nucleic acid (TNA), or Xeno nucleic acid. The RNA may be a subpopulation of RNA, such as mRNA, tRNA, rRNA, miRNA, or siRNA. Preferably the nucleic acid is DNA.

The target or feature of interest may be any feature of a nucleic acid. The feature may be a mutation. For example and without limitation, the feature may be an insertion, deletion, substitution, inversion, amplification, duplication, translocation, or polymorphism. The feature may be a nucleic acid from an infectious agent or pathogen. For example, the nucleic acid sample may be obtained from an organism, and the feature may contain a sequence foreign to the genome of that organism.

The target nucleic acid may be from a sub-population of nucleic acid within the nucleic acid sample. For example, the target nucleic acid may contain cell-free DNA, such as cell-free fetal DNA or circulating tumor DNA. In some embodiments, the sample includes plasma from the subject and the target nucleic acid is cell-free DNA (cfDNA). The plasma may be maternal plasma and the target may be of fetal DNA. In certain embodiments, the sample includes plasma from the subject and the target is circulating tumor DNA (ctDNA). In some embodiments, the sample includes at least one circulating tumor cell from a tumor and the target is tumor DNA from the tumor cell.

According to an aspect of the invention, methods for primer extension-mediated polynucleotide enrichment are provided. The methods include contacting the polynucleic acid molecule with at least one primer that binds to a sequence of the polynucleic acid molecule flanking the region of interest, or target nucleic acid. The primer is extended using a polymerase and one or more types of modified nucleotide triphosphates. Extension of the primer with the modified nucleotide triphosphates generates a modified polynucleic acid molecule that is resistant to nuclease-mediated cleavage. The polynucleic acid molecule and the modified polynucleic acid molecule may be contacted with a nuclease to digest the polynucleic acid molecule 5' and 3' to the modified polynucleic acid. Therefore, the polynucleic acid molecule outside of the region of interest is digested, and the target nucleic acid is isolated. In some embodiments, two primers are used.

In certain embodiments, methods for enrichment of a polynucleic acid molecule region of interest that has at least one 5' overhang are provided. The methods include contacting the polynucleic acid molecule with at least one polymerase. The primer is extended using a polymerase and one or more types of modified nucleotide triphosphates. Extension of the primer with the one or more types of modified nucleotide triphosphates generates a modified polynucleic acid molecule that lacks a 5' overhang and that is resistant to nuclease-mediated cleavage. The polynucleic acid molecule and the modified polynucleic acid molecule may be contacted with a nuclease. As such, the polynucleic acid molecule outside of the region of interest is digested, thereby isolating the region of interest, or target nucleic acid.

In certain embodiments, methods for enrichment of a double-stranded polynucleic acid molecule region of interest are provided. The methods include contacting the polynucleic acid molecule with at least one CRISPR/Cas complex that binds to a sequence of the double-stranded polynucleic acid molecule flanking the region of interest. Contacting the polynucleic acid molecule with the CRISPR/Cas complex generates at least one double-strand break flanking the region of interest. The polynucleic acid molecule with at least one double-strand break may be contacted with a ligase and a double-stranded oligonucleotide comprising modified nucleotides. Contacting the polynucleic acid molecule with at least one double-strand break with a ligase and a double-stranded oligonucleotide covalently links the region of interest with the double stranded oligonucleotide and generates a modified polynucleic acid molecule that is resistant to nuclease-mediated cleavage. The polynucleic acid molecule and the modified polynucleic acid molecule may be contacted with a nuclease. The polynucleic acid molecule outside of the region of interest is digested, thereby isolating the target nucleic acid.

In some embodiments, the modified polynucleic acid molecule includes at least one phosphorothioate linkage, N3' phosphoramidate linkage, boranophosphate internucleotide linkage, or phosphonoacetate linkage.

In some embodiments, at least one of the one or more types of modified nucleotide triphosphates is an alpha-phosphorothioate nucleotide triphosphate. In some embodiments, the alpha-phosphorothioate nucleotide triphosphate is 2'-Deoxyadenosine-5'-O-(1-Thiotriphosphate), 2'-Deoxycytidine-5'-O-(1-Thiotriphosphate), 2'-Deoxyguanosine-5'-O-(1-Thiotriphosphate), 2'-Deoxythymidine-5'-O-(1-Thiotriphosphate), Adenosine-5'-O-(1-Thiotriphosphate), Cytidine-5'-O-(1-Thiotriphosphate), Guanosine-5'-O-(1-Thiotriphosphate), Uridine-5'-O-(1-Thiotriphosphate), 2',3*-Dideoxyadenosine-5'-O-(1-Thiotriphosphate), 2',3'-Dideoxycytidine-5'-O-(1-Thiotriphosphate), 2',3*-Dideoxyguanosine-5'-O-(1-Thiotriphosphate), 3'-Deoxythymidine-5'-O-(1-Thiotriphosphate), 3'-Azido-2',3'-dideoxythymidine-5'-O-(1-Thiotriphosphate), 2',3*-Dideoxyuridine-5'-O-(1-Thiotriphosphate), 2'-Deoxyadenosine-5'-O-(1-Boranotriphosphate), 2'-Deoxycytidine-5'-O-(1-Boranotriphosphate), 2'-Deoxyguanosine-5'-O-(1-Boranotriphosphate), or 2'-Deoxythymidine-5'-O-(1-Boranotriphosphate). In some embodiments, the alpha-phosphorothioate nucleotide triphosphate is 2'-Deoxycytidine-5'-O-(1-Thiotriphosphate).

In some embodiments, at least one of the one or more types of modified nucleotide triphosphates is a morpholino triphosphate. In some embodiments, at least one of the one or more types of modified nucleotide triphosphates is a peptide nucleic acid or a peptide nucleic acid analog.

In some embodiments, at least one of the one or more types of modified nucleotide triphosphates is a sugar modified nucleotide triphosphate. In some embodiments, the sugar modified nucleotide triphosphate is a 2' O-methyl modified nucleotide triphosphate. In some embodiments, the 2' O-methyl modified nucleotide triphosphate is 2'-OMethyladenosine-5'-Triphosphate, 2'-O-Methylcytidine-5'-Triphosphate, 2'-O-Methylguanosine-5'-Triphosphate, 2'-0-Methyluridine-5'-Triphosphate, 2'-O-Methylinosine-5'-Triphosphate, 2'-O-Methyl-2-aminoadenosine-5'-Triphosphate, 2'-O-Methylpseudouridine-5'-Triphosphate, 2'-O-Methyl-5-methyluridine-5'-Triphosphate, or 2'-O-Methyl-N6-Methyladenosine-5'-Triphosphate. In some embodiments, the sugar modified nucleotide triphosphate is a 2' fluoro-modified nucleotide triphosphate. In some embodiments, the 2' fluoro-modified nucleotide triphosphate is 2'-Fluoro-2'-deoxyadenosine-5'-Triphosphate, 2'-Fluoro-2'-deoxycytidine-5'-Triphosphate, 2'-Fluoro-2'-deoxyguanosine-5'-Triphosphate, 2'-Fluoro-2'-deoxyuridine-5'-Triphosphate, or 2'-Fluoro-thymidine-5'-Triphosphate.

In certain embodiments, the phosphorothioates enzymatically incorporated are stereo-isomerically pure R or S stereoisomers. In certain embodiments, the phosphorothioates enzymatically incorporated are a racemic mixture of the two stereoisomers.

According to another aspect, methods for enrichment of a polynucleic acid molecule region of interest are provided. The methods include contacting the polynucleic acid molecule with at least one primer that binds to a sequence of the polynucleic acid molecule flanking the region of interest. The primer is extended using a polymerase and nucleotide triphosphates. The extended region of interest is dephosphorylated using a phosphatase, wherein the dephosphorylation of the region of interest generates a modified polynucleic acid molecule that is resistant to nuclease-mediated cleavage. The polynucleic acid molecule and the modified polynucleic acid molecule are contacted with a nuclease to digest the polynucleic acid molecule outside of the region of interest. The digestion step isolates the target nucleic acid, or region of interest. In some embodiments, two primers are used.

In certain embodiments, one end of the target nucleic acid will be protected from nuclease degradation using the modified nucleotides. The other end of the target nucleic acid may be protected from nuclease degradation using a protein that binds to the target in a sequence specific manner. According to an embodiment, methods for enrichment of a double-stranded polynucleic acid molecule region of interest are provided. The methods include contacting the polynucleic acid molecule with at least one CRISPR/Cas complex that binds to a sequence of the double-stranded polynucleic acid molecule flanking the region of interest. Contacting the polynucleic acid molecule with the CRISPR/Cas complex generates at least one double-strand break flanking the region of interest. The polynucleic acid molecule with at least one double-strand break may be dephosphorylated using a phosphatase, wherein the dephosphorylation of the polynucleic acid molecule with at least one double-strand break generates a modified polynucleic acid molecule that is resistant to nuclease-mediated cleavage. The polynucleic acid molecule and the modified polynucleic acid molecule may be contacted with a nuclease, thereby digesting the polynucleic acid molecule outside of the region of interest. Thus, the region of interest, or target nucleic acid, is isolated.

In some embodiments, the polynucleic acid molecule region of interest is between 100 to 10,000 nucleotides or base pairs in length. In some embodiments, the polynucleic acid molecule is contained in or isolated from a biological sample. In some embodiments, the biological sample comprises blood or tissue. In some embodiments, the biological sample comprises microorganisms. In some embodiments, the biological sample is purified. In some embodiments, the polynucleic acid molecule is DNA. In some embodiments, the DNA is genomic DNA.

DETAILED DESCRIPTION

Figure 1:
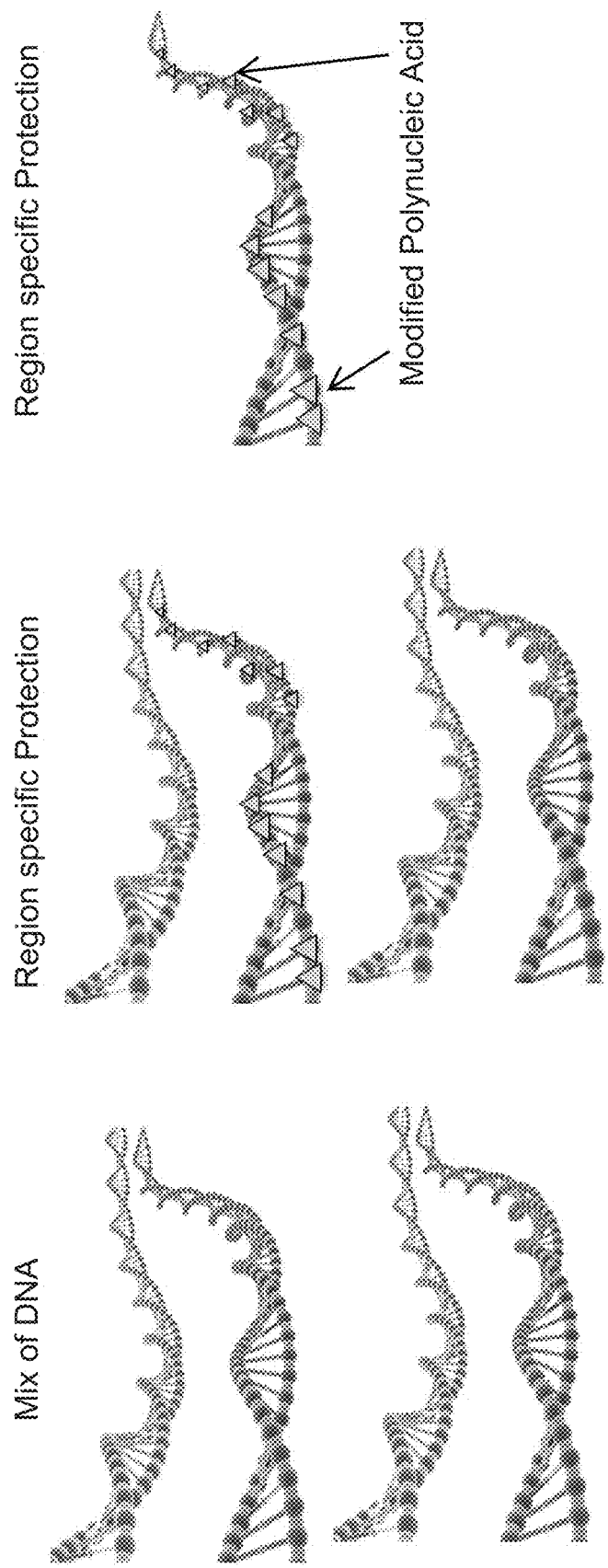
FIG. 1 shows primer extension-mediated polynucleic acid enrichment. Extension replication of a polynucleic acid molecule (represented here as dsDNA) region of interest using modified triphosphates, a primer that binds to a sequence flanking the region of interest (a single primer in this instance), and a polymerase generates a modified polynucleic acid molecule that is resistant to nuclease-mediated cleavage. Subsequent exposure of the polynucleic acid mixture to a nuclease, such as an exonuclease, results in digestion of the unprotected polynucleic acid molecules and, thus, enrichment of the region of interest.

For many polynucleic acid sequencing applications, enrichment is used to reduce or eliminate polynucleic acid molecules that are not of interest and to select for those that are of interest. Applications wherein enrichment is common include the examination of specific copy number variants, single nucleotide polymorphisms, or DNA rearrangements, and the examination of specific "classes" of polynucleic acid molecules (e.g., messenger RNA, noncoding RNA, genomic DNA, exonic genomic DNA, mitochondrial DNA, etc.). By targeting a specific polynucleic acid molecule, one can obtain greater depth of sequencing coverage for regions of interest and increase sampling numbers, thereby reducing the time and costs associated with sequencing.

Previously described enrichment methodologies can be roughly divided into two categories, hybridization-based strategies and PCR amplification-based strategies, based on how desired polynucleic acid sequences are "captured" or selected from a large polynucleic acid pool (Kozarewa et al., Curr. Protoc. Mol. Biol. 112, 1-23 (2015); Altmuller et al., Biol. Chem. 395, 231-37 (2014); Mertes et al., Brief Funct. Genomics 10, 374-86 (2011)). Hybridization-based strategies involve the use of DNA or RNA probes or "baits" which are single stranded oligonucleotides that are complementary to the region of interest (or a region flanking the area of interest). These probes hybridize to the region of interest in solution or on a solid support so that one can physically isolate the region of interest and, thereby, enrich the region of interest relative to other regions. PCR-based strategies involve the use of specific primer pairs that are complementary to the region of interest (or a region flanking the area of interest). These primer pairs are used to amplify large amounts of the region of interest and, thereby, enrich the region of interest relative to other regions.

Described herein are novel polynucleic acid molecule enrichment methodologies that are nuclease protection-based strategies, unlike previously described hybridization-based strategies or PCR amplification-based strategies. Nuclease protection-based strategies involve the protection of a polynucleic acid molecule region of interest, or target nucleic acid, from nuclease-mediated degradation by selective blockage. Application of these nuclease protection-based enrichment methodologies include polynucleic acid sequencing on all long molecule sequencing platforms (e.g., MiSeq (Illumina), NextSeq (Illumina), HiSeq (Illumina), Ion Torrent PGM (Life Technologies), Ion Torrent Proton (Life Technologies), ABI SOLiD (Life Technologies), 454 GS FLX+ (Roche), 454 GS Junior (Roche), etc.) as well as short read sequencing platforms.

The invention provides methods of isolating target nucleic acids within a sample. The target nucleic acids in the sample may be protected from nuclease degradation, for example by creating a modified polynucleotide using polymerase and modified nucleotides resistant to nuclease degradation or by binding proteins which are resistant to nuclease degradation to the target in a sequence-specific manner. The protected target nucleic acid may be isolated.

Certain embodiments of the invention provide extension-mediated polynucleic acid molecule enrichment. In one aspect, a polynucleic acid region of interest, or target nucleic acid, is selectively blocked from nuclease digestion by extension replication of the region of interest using modified nucleotide triphosphates. Extension of a polynucleic acid molecule region of interest using modified triphosphates generates a modified polynucleic acid molecule that is resistant to nuclease-mediated cleavage. Subsequent exposure of the polynucleic acid mixture to a nuclease results in digestion of the unprotected polynucleic acid molecules and, thus, enrichment of the region of interest (FIG. 1).

In certain embodiments, enrichment of a polynucleic acid region of interest comprises protecting the region of interest by contacting the polynucleic acid molecule with at least one primer that binds to a sequence of the polynucleic acid molecule flanking the region of interest of the polynucleic acid molecule. The primer may be extended in the region of interest sequence using a polymerase and one or more types of modified nucleotide triphosphates, wherein extension of the primer with the one or more types of modified nucleotide triphosphates generates a modified polynucleic acid molecule resistant to nuclease-mediated cleavage. The polynucleic acid molecule and the modified nucleic acid molecule may be contacted with a nuclease, such as an exonuclease, to digest the polynucleic acid molecule 5' and 3' to the modified polynucleic acid. The polynucleic acid molecule outside of the region of the polynucleic acid molecule is thereby digested.

In an embodiment, enrichment of a double stranded polynucleic acid molecule region of interest comprises contacting the polynucleic acid molecule with at least one CRISPR/Cas complex that binds to a sequence of the double stranded polynucleic acid molecule flanking the region of interest. Contacting the polynucleic acid molecule with the at least one CRISPR/Cas complex generates at least one double strand break flanking the region of interest. The polynucleic acid molecule may be dephosphorylated with at least one double strand break using a phosphatase, wherein dephosphorylation of the polynucleic acid molecule with at least one double strand break generates a modified polynucleic acid molecule that is resistant to nuclease-mediated cleavage. The polynucleic acid molecule and the modified polynucleic acid molecule may be contacted with a nuclease, thereby digesting the polynucleic acid molecule outside of the region of interest.

In certain embodiments, enrichment of a polynucleic acid molecule region of interest comprises contacting the polynucleic acid molecule with at least one primer that binds to a sequence of the polynucleic acid molecule flanking the region of interest. The primer is extended using a polymerase and nucleotide triphosphates. The extended region of interest may be dephosphorylated using a phosphatase, wherein the dephosphorylation of the region of interest generates a modified polynucleic acid molecule that is resistant to nuclease-mediated cleavage. The polynucleic acid molecule and the modified polynucleic acid molecule may be contacted with a nuclease, thereby digesting the polynucleic acid molecule outside of the region of interest.

In some embodiments two primers are used. In some embodiments, the two primers allow for PCR amplification of the region of interest. In some cases, only a small number of PCR cycles is performed (e.g., 1, 2, 3, 4 or 5). Thus, the enrichment of the region of interest is not the result of amplification of the region of interest, but rather results from removal of sequences other than the region of interest by nuclease-mediated degradation.

In certain embodiments, enrichment of a polynucleic acid molecule region of interest that has at least one 5' overhang comprises protecting the region of interest by contacting the polynucleic acid molecule with at least one polymerase. The 3' end is extended to fill in the overhang using a polymerase and one or more types of modified nucleotide triphosphates. Extension of the 3' end to fill in the overhang with the one or more types of modified nucleotide triphosphates generates a modified polynucleic acid molecule that lacks a 5' overhang. The modified polynucleic acid molecule is resistant to nuclease-mediated cleavage. The polynucleic acid molecule and the modified polynucleic acid molecule may be contacted with a nuclease, thereby digesting the polynucleic acid molecule outside of the region of interest.

In one aspect of the invention, a polynucleic acid region of interest, or target nucleic acid, is selectively blocked from nuclease digestion following CRISPR/Cas digestion. In certain embodiments, enrichment of a double stranded polynucleic acid molecule region of interest comprises contacting the polynucleic acid molecule with at least one CRISPR/Cas complex that binds to a sequence of the double stranded polynucleic acid molecule flanking the region of interest. Contacting the polynucleic acid molecule with the at least one CRISPR/Cas complex generates at least one double strand break flanking the region of interest. The polynucleic acid molecule with at least one double strand break may be contacted with a ligase and a double stranded oligonucleotide comprising modified nucleotides. Contacting the polynucleic acid molecule with at least one double strand break with a ligase and a double stranded oligonucleotide covalently links the region of interest with the double stranded oligonucleotide and generates a modified polynucleic acid molecule that is resistant to nuclease-mediated cleavage. The polynucleic acid molecule and the modified polynucleic acid molecule may be contacted with a nuclease, thereby digesting the polynucleic acid molecule outside of the region of interest. In some embodiments, a single-stranded oligonucleotide can be ligated in place of the double-stranded oligonucleotide to generate a modified polynucleic acid molecule that is resistant to nuclease-mediated cleavage. Optionally, the overhang created by the single-stranded oligonucleotide can be filled in using a polymerase.

In an embodiment, a sample of nucleic acids including a target nucleic acid is provided. The target nucleic acid is protected by allowing proteins to bind to sequences at the ends of the target nucleic acid. The target nucleic acid may be a portion of larger nucleic acid molecule, and the ends of the target nucleic acid may not be the ends of a nucleic acid molecule, i.e., the ends may not be free 5' phosphate groups or free 3' OH groups. Binding of the proteins to the ends of the target nucleic acid provides protection against exonuclease digestion. Nucleic acids in the sample are then digested by for, example, an exonuclease, but the target nucleic acid is protected from digestion. The target nucleic acid may then be detected by any suitable means.

In certain embodiments, methods of the invention may further comprise detecting the target nucleic acid. One method for detection of the modified nucleotides and protein-bound nucleic acids is immunomagnetic separation. Magnetic or paramagnetic particles are coated with an antibody that binds the protein bound to the segment, and a magnetic field is applied to separate particle-bound segment from other nucleic acids. Methods of immunomagnetic purification of biological materials such as cells and macromolecules are known in the art and described in, for example, U.S. Pat. No. 8,318,445; Safarik and Safarikova, Magnetic techniques for the isolation and purification of proteins and peptides, Biomagn Res Technol. 2004; 2:7, doi: 10.1186/1477-044X-2-7, the contents of each of which are incorporated herein by reference. The antibody may be a full-length antibody, a fragment of an antibody, a naturally occurring antibody, a synthetic antibody, an engineered antibody, or a fragment of the aforementioned antibodies. Alternatively or additionally, the particles may be coated with another protein-binding moiety, such as an aptamer, peptide, receptor, ligand, or the like.

Chromatographic methods may be used for detection. In such methods, the sample is applied to a column, and the target nucleic acid is separated from other nucleic acids based on a difference in the properties of the segment and the other nucleic acids. Size exclusion chromatography is useful for separating molecules based on differences in size and thus is useful when the segment is larger than the residual nucleic acids left from the digestion step. Methods of size exclusion chromatography are known in the art and described in, for example, Ballou, David P.; Benore, Marilee; Ninfa, Alexander J. (2008). Fundamental laboratory approaches for biochemistry and biotechnology (2nd ed.). Hoboken, N.J.: Wiley. p. 129. ISBN 9780470087664; Striegel, A. M.; and Kirkland, J. J.; Yau, W. W.; Bly, D. D.; Modern Size Exclusion Chromatography, Practice of Gel Permeation and Gel Filtration Chromatography, 2nd ed.; Wiley: NY, 2009, the contents of each of which are incorporated herein by reference.

Ion exchange chromatography uses an ion exchange mechanism to separate analytes based on their respective charges. Thus, ion exchange chromatography can be used because the proteins bound to the segment impart a differential charge as compared to other nucleic acids. Methods of ion exchange chromatography are known in the art and described in, for example, Small, Hamish (1989). Ion chromatography. New York: Plenum Press. ISBN 0-306-43290-

0; Tatjana Weiss, and Joachim Weiss (2005). Handbook of Ion Chromatography. Weinheim: Wiley-VCH. ISBN 3-527-28701-9; Gjerde, Douglas T.; Fritz, James S. (2000). Ion Chromatography. Weinheim: Wiley-VCH. ISBN 3-527-29914-9; and Jackson, Peter; Haddad, Paul R. (1990). Ion chromatography: principles and applications. Amsterdam: Elsevier. ISBN 0-444-88232-4, the contents of each of which are incorporated herein by reference.

Adsorption chromatography relies on difference in the ability of molecule to adsorb to a solid phase material. Larger nucleic acid molecules are more adsorbent on stationary phase surfaces than smaller nucleic acid molecules, so adsorption chromatography is useful when the segment is larger than the residual nucleic acids left from the digestion step. Methods of adsorption chromatography are known in the art and described in, for example, Cady, 2003, Nucleic acid purification using microfabricated silicon structures. Biosensors and Bioelectronics, 19:59-66; Melzak, 1996, Driving Forces for DNA Adsorption to Silica in Perchlorate Solutions, J Colloid Interface Sci 181:635-644; Tian, 2000, Evaluation of Silica Resins for Direct and Efficient Extraction of DNA from Complex Biological Matrices in a Miniaturized Format, Anal Biochem 283:175-191; and Wolfe, 2002, Toward a microchip-based solid-phase extraction method for isolation of nucleic acids, Electrophoresis 23:727-733, each incorporated by reference.

Another method for detection is gel electrophoresis. Gel electrophoresis allows separation of molecules based on differences in their sizes and is thus useful when the segment is larger than the residual nucleic acids left from the digestion step. Methods of gel electrophoresis are known in the art and described in, for example, Tom Maniatis; E. F. Fritsch; Joseph Sambrook. "Chapter 5, protocol 1". Molecular Cloning—A Laboratory Manual. 1 (3rd ed.). p. 5.2-5.3. ISBN 978-0879691363; and Ninfa, Alexander J.; Ballou, David P.; Benore, Marilee (2009). fundamental laboratory approaches for biochemistry and biotechnology. Hoboken, N.J.: Wiley. p. 161. ISBN 0470087668, the contents of which are incorporated herein by reference.

The proteins that bind to ends of the target nucleic acid may be any proteins that bind a nucleic acid in a sequence-specific manner. The protein may be a programmable nuclease. For example, the protein may be a CRISPR-associated (Cas) endonuclease, zinc-finger nuclease (ZFN), transcription activator-like effector nuclease (TALEN), or RNA-guided engineered nuclease (RGEN). Programmable nucleases and their uses are described in, for example, Zhang, 2014, "CRISPR/Cas9 for genome editing: progress, implications and challenges", Hum Mol Genet 23 (R1):R40-6; Ledford, 2016. CRISPR: gene editing is just the beginning, Nature. 531 (7593): 156-9; Hsu, 2014, Development and applications of CRISPR-Cas9 for genome engineering, Cell 157(6):1262-78; Boch, 2011, TALEs of genome targeting, Nat Biotech 29(2):135-6; Wood, 2011, Targeted genome editing across species using ZFNs and TALENs, Science 333(6040):307; Carroll, 2011, Genome engineering with zinc-finger nucleases, Genetics Soc Amer 188(4):773-782; and Urnov, 2010, Genome Editing with Engineered Zinc Finger Nucleases, Nat Rev Genet 11(9):636-646, each incorporated by reference. The protein may be a catalytically inactive form of a nuclease, such as a programmable nuclease described above. The protein may be a transcription activator-like effector (TALE). The protein may be complexed with a nucleic acid that guides the protein to an end of the segment. For example, the protein may be a Cas endonuclease-guide RNA complex.

The unprotected nucleic acid may be digested by any suitable means. Preferably, the unprotected nucleic acid is digested by one or more exonucleases.

The term "nucleic acid," as used herein refers to a compound comprising a nucleobase and an acidic moiety (e.g., a nucleoside, a nucleotide, or a polymer of nucleotides). As used herein, the terms "polynucleic acid" or "polynucleic acid molecule" are used interchangeably and refer to polymeric nucleic acids (e.g., nucleic acid molecules comprising three or more nucleotides that are linked to each other via a phosphodiester linkage).

Polynucleic acid molecules have various forms. In some embodiments, the polynucleic acid molecule is DNA. In some embodiments, the polynucleic acid molecule is double-stranded DNA. For example, in some embodiments, the DNA is genomic DNA. In other embodiments, the polynucleic acid molecule is single-stranded DNA. In some embodiments, the polynucleic acid molecule is RNA. In some embodiments, the polynucleic acid molecule is double-stranded RNA. In other embodiments, the polynucleic acid molecule is single-stranded RNA.

In certain embodiments, the polynucleic acid molecule is contained in or isolated from a biological sample. As used herein, the term "contained in" refers to a polynucleic acid molecule that is within a biological sample. For example, in certain embodiments, a polynucleic acid region of interest is protected from nuclease-mediated degradation while the polynucleic acid is within a living biological sample. In other embodiments, a polynucleic acid region of interest is protected from nuclease-mediated degradation while the polynucleic acid is within a lysed biological sample.

The term "isolated," as used herein refers to the separation of a polynucleic acid component of a biological sample from other molecules of a biological sample. For example, in certain embodiments, a polynucleic acid region of interest is protected from nuclease mediated degradation after the polynucleic acid component of a biological sample has been separated from other molecules of a biological sample. Methods of isolating polynucleic acid components from a biological sample are well known to those of skill in the art. Isolation can include partial purification of a polynucleic acid component of a biological sample.

As used herein, the term "biological sample" may refer a cell or a combination of cells. The term "cell" may refer to a prokaryotic cell or a eukaryotic cell. "Prokaryotic cells" include bacteria and archaea. In certain embodiments, the prokaryotic cell is a bacteria of a phyla selected from Actinobacteria, Aquificae, Armatimonadetes, Bacteroidetes, Caldiserica, Chlamydiae, Chloroflexi, Chrysiogenetes, Cyanobacteria, Deferribacteres, Deinococcus-Thermus, Dictyoglomi, Elusimicrobia, Fibrobacteres, Firmicutes, Fusobacteria, Gemmatimonadetes, Nitrospirae, Planctomycetes, Proteobacteria, Spirochaetes, Synergistets, Tenericutes, Thermodesulfobacteria, and Thermotogae. In some embodiments the prokaryotic cell is an archaea of a phyla selected from Euryarcheota, Crenarcheota, Nanoarchaeota, Thaumarchaeota, Aigarchaeota, Lokiarchaeota, Thermotogae, and Tenericutes. In certain embodiments, the eukaryotic cell is a member of a kingdom selected from Protista, Fungi, Plantae, or Animalia.

In certain embodiments, the biological sample comprises independent cells (i.e., cells that exist in a single cellular state). In certain embodiments, the biological sample comprises cells that exist as part of a multicellular organism. For example, a cell may be located in a transgenic animal or transgenic plant. In some embodiments, the biological sample is a microorganism. In certain embodiments, a biological sample is uniform (e.g., made up of the same cell types). In certain embodiments, a biological sample is made up of many cell types. In some embodiments, the biological sample comprises blood (or components thereof) or tissue (or components thereof).

The term "biological sample" may also refer to a virus. The term "virus" may refer to a DNA virus (e.g., Adenoviridae, Papovaviridae, Parvoviridae, Herpesviridae, Poxiridae, Hepadnaviridae, Anelloviridae, etc) or an RNA virus (e.g., Reoviridae, Picornaviridae, Calciviridae, Togaviridae, Arenaviridae, Flaviviridae, Orthomyxoviridae, Paramyxoviridae, Bunyaviridae, Rhabdoviridae, Filoviridae, Coronaviridae, Astroviridae, Bornoviridae, Arteriviridae, Hepeviridae, etc.).

The term "virus" may also refer to a phage. As used herein, the term "phage" refers to both bacteriophages and archaeophages. "Bacteriophage" refers to a virus that infects bacteria. "Archaeophage" refers to a virus that infects archaea. Bacteriophages and archaeophages are obligate intracellular parasites that multiply inside a host cell by making use of some or all of the cell's biosynthetic machinery. In some embodiments a phage is a member of an order selected from Caudovirales, Microviridae, Corticoviridae, Tectiviridae, Leviviridae, Cystoviridae, Inoviridae, Lipothrixviridae, Rudiviridae, Plasmaviridae, and Fuselloviridae. In certain embodiments, the phage is a member of the order Caudoviralesand is a member of a family selected from Myoviridae, Siphoviridae, and Podoviridae.

The nucleic acid may be any naturally-occurring or artificial nucleic acid. The nucleic acid may be DNA, RNA, hybrid DNA/RNA, peptide nucleic acid (PNA), morpholine and locked nucleic acid (LNA), glycol nucleic acid (GNA), threose nucleic acid (TNA), or Xeno nucleic acid. The RNA may be a subpopulation of RNA, such as mRNA, tRNA, rRNA, miRNA, or siRNA. Preferably the nucleic acid is DNA.

The feature of interest may be any feature of a nucleic acid. The feature may be a mutation. For example and without limitation, the feature may be an insertion, deletion, substitution, inversion, amplification, duplication, translocation, copy number variation, or polymorphism. The feature may be a nucleic acid from an infectious agent or pathogen. For example, the nucleic acid sample may be obtained from an organism, and the feature may contain a sequence foreign to the genome of that organism.

The target nucleic acid may be from a sub-population of nucleic acid within the nucleic acid sample. For example, the segment may contain cell-free DNA, such as cell-free fetal DNA or circulating tumor DNA.

The nucleic acid sample may come from any source. For example, the source may be an organism, such as a human, non-human animal, plant, or other type of organism. The sample may be a tissue sample from an animal, such as blood, serum, plasma, skin, urine, saliva, semen, feces, phlegm, conjunctiva, gastrointestinal tract, respiratory tract, vagina, placenta, uterus, oral cavity or nasal cavity. The sample may be a liquid biopsy. The nucleic acid sample may come from an environmental source, such as a soil sample or water sample, or a food source, such as a food sample or beverage sample. The sample may comprise nucleic acids that have been isolated, purified, or partially purified from a source. Alternatively, the sample may not have been processed.

Certain embodiments provide a method for isolating a target nucleic acid in a sample that includes DNA from a subject. The DNA may be any suitable DNA. In preferred embodiments, the DNA includes cell-free DNA, such as circulating tumor DNA (ctDNA) or fetal DNA from maternal blood or plasma. The sample may include plasma from the subject in which the segment is cell-free DNA (cfDNA). In some embodiments, the sample includes maternal plasma and fetal DNA. In certain embodiments, ctDNA is in the sample. In some embodiments, the sample includes at least one circulating tumor cell from a tumor and the segment comprises tumor DNA from the tumor cell.

As used herein, the term "region of interest" refers to the region of a polynucleic acid that one seeks to enrich relative to other polynucleic acid regions. The length of regions of interest can vary. For example, in some embodiments, the polynucleic acid molecule region of interest is at least 10,000 nucleotides or base pairs in length, such as 20,000, 25,000, 30,000, 40,000, 50,000, 60,000, 70,000, 80,000, 90,000, 100,000, or more nucleotides or base pairs in length. In other embodiments, the polynucleic acid molecule region of interest is as few as five nucleotides or base pairs in length.

The term "nuclease," as used herein refers to an agent (e.g., a protein) capable of cleaving a phosphodiester bond connecting two nucleotide residues in a polynucleic acid molecule. The term "nuclease" includes endonucleases, exonucleases, and agents that exhibit both endonuclease and exonuclease activity. As used herein, the term endonuclease refers to a nuclease that is capable of cleaving a phosphodiester bond within a polynucleic acid molecule. Specific endonucleases include, but are not limited to, restriction endonucleases (e.g., EcoRI, BamHI, HindIII, etc.), DNase I, DNase II, Micrococcal nuclease, Mung Bean nuclease, RNase A, RNase H, RNase III, RNase L, RNase P, RNase PhyM, RNase T1, RNase T2, RNase U2, RNase V, and RNA-guided endonucleases (e.g., CRISPR/Cas proteins). As used herein, the term exonuclease refers to a nuclease that is capable of cleaving a phosphodiester bond at the end of a polynucleic acid molecule.

Specific exonucleases include, but are not limited to, T7 exonuclease, T5, exonuclease, lambda exonuclease, Exonucleases I, Exonuclease III, Exonuclease V, Exonuclease VII, Exonuclease VIII, Exonuclease T, RNase PH, RNase R, RNase T, Oligoribonuclease, Exoribonuclease I, Exoribonuclease II, and PNPase. In certain embodiments, the polynucleic acid molecule and the modified polynucleic acid molecule are contacted with at least one endonuclease. In certain embodiments, the polynucleic acid molecule and the modified polynucleic acid molecule are contacted with at least one exonuclease. In certain embodiments, the polynucleic acid molecule and the modified polynucleic acid molecule are contacted with at least one agent that exhibits endonuclease and exonuclease activity. In certain embodiments, the polynucleic acid molecule and the modified polynucleic acid molecule is contacted with a combination of at least one endonuclease, at least one exonuclease, and/or at least one agent that exhibits endonuclease and exonuclease activity.

As used herein, the terms "protection" or "protecting" with respect to a region of interest refer to a decrease in the region of interest's susceptibility to nuclease-mediated cleavage by at least 20%, 25%, 30%, 40%, 50%, 60%, 70%, 80%, 90%, or up to 100% relative to other polynucleic acid regions. Methods of measuring and comparing levels of nuclease-mediated cleavage are known to those skilled in the art. In certain embodiments, the region of interest is protected from all nucleases. In certain embodiments, the region of interest is protected from all exonucleases. In certain embodiments, the region of interest is protected from all endonucleases. In certain embodiments, the region of interest is protected from a subset of exonucleases or endonucleases. In certain embodiments, the region of interest is protected from a single exonuclease or endonuclease.

As used herein, the term "primer" refers to a relatively short single-stranded RNA or single-stranded DNA molecule that complements a region of a polynucleic acid and serves as a starting point for polymerase-mediated polynucleic acid synthesis. Because the polynucleic acid sequence that a primer may compliment will vary, the composition of primers encompassed herein is broad. Likewise, the length of a primer can vary. Generally a primer is 18-30 nucleotides or base pairs in length. However, in certain embodiments, a primer is as short as 5 nucleotides or base pairs in length. In certain embodiments, the primer is as long as 200 nucleotides or base pairs in length. In certain embodiments, a primer comprises a modified polynucleic acid molecule. For example, the naturally occurring phosphodiester backbone of a primer can be partially or completely modified with phosphorothioate, phosphorodithioate, or methylphosphonate internucleotide linkage modifications. A primer may also comprise modified nucleoside bases or modified sugars. In addition, a primer may be labelled (e.g., with a fluorescent moiety, biotin, etc.). In certain embodiments, a primer is modified so as to increase its stability. In certain embodiments, a primer is modified to facilitate the isolation of the polynucleic acid molecule generated through polymerase-mediated extension of the primer.

The term, "modified nucleotide triphosphate" as used herein refers to any nucleotide triphosphate compound whose composition differs from natural occurring nucleotide triphosphates and whose incorporation into a polynucleic acid molecule renders the polynucleic acid molecule more resistant to nuclease-mediated cleavage relative to a polynucleic acid molecule that does not have incorporated modified bases. Naturally occurring nucleoside triphosphates include adenosine triphosphate, guanosine triphosphate, cytidine triphosphate, 5-methyluridine triphosphate, and uridine triphosphate. Examples of modified nucleotides triphosphates that meet these requirements are known to those of skill in the art (Deleavey and Damha Chem. Biol. 19, 937-54 (2012); Monia et al. J. Biol. Chem. 271, 14533-40 (1996)). In certain embodiments, at least one of the one or more types of modified nucleotide triphosphates is an alpha-phosphorothioate nucleotide triphosphate. In certain embodiments, the alpha-phosphorothioate nucleotide triphosphate is selected from 2'-Deoxyadenosine-5'-O-(1-Thiotriphosphate), 2'-Deoxycytidine-5'-O-(1-Thiotriphosphate), 2'-Deoxyguanosine-5'-O-(1-Thiotriphosphate), 2'-Deoxythymidine-5'-O-(1-Thiotriphosphate), Adenosine-5'-O-(1-Thiotriphosphate), Cytidine-5'-O-(1-Thiotriphosphate), Guanosine-5'-O-(1-Thiotriphosphate), Uridine-5'-O-(1-Thiotriphosphate), 2',3*-Dideoxyadenosine-5'-O-(1-Thiotriphosphate), 2',3'-Dideoxycytidine-5'-O-(1-Thiotriphosphate), 2',3*-Dideoxyguanosine-5'-O-(1-Thiotriphosphate), 3'-Deoxythymidine-5'-O-(1-Thiotriphosphate), 3'-Azido-2',3'-dideoxythymidine-5'-O-(1-Thiotriphosphate), 2',3*-Dideoxyuridine-5'-O-(1-Thiotriphosphate), 2'-Deoxyadenosine-5'-O-(1-Boranotriphosphate), 2'-Deoxycytidine-5'-O-(1-Boranotriphosphate), 2'-Deoxyguanosine-5'-O-(1-Boranotriphosphate), and 2'-Deoxythymidine-5'-O-(1-Boranotriphosphate). In certain embodiments, the alpha-phosphorothioate is 2'-Deoxycytidine-5'-O-(1-Thiotriphosphate).

In certain embodiments, at least one of the one or more types of modified nucleotide triphosphates is a morpholino triphosphate. In certain embodiments, at least one of the one or more types of modified nucleotide triphosphates is a peptide nucleic acid or a peptide nucleic acid analog.

In certain embodiments, at least one of the one or more types of modified nucleotide triphosphates is a sugar modified nucleotide triphosphate. In certain embodiments, the sugar modified nucleotide triphosphate is a 2' O-methyl modified nucleotide triphosphate. In certain embodiments, the 2' O-methyl modified nucleotide triphosphate is selected from 2'-OMethyladenosine-5'-Triphosphate, 2'-O-Methylcytidine-5'-Triphosphate, 2'-OMethylguanosine-5'-Triphosphate, 2'-O-Methyluridine-5'-Triphosphate, 2'-O-Methylinosine-5'-Triphosphate, 2'-O-Methyl-2-aminoadenosine-5'-Triphosphate, 2'-O-Methylpseudouridine-5'-Triphosphate, 2'-O-Methyl-5-methyluridine-5'-Triphosphate, and 2'-O-Methyl-N6-Methyladenosine-5'-Triphosphate.

In certain embodiments, the sugar modified nucleotide triphosphate is a 2' fluoro-modified nucleotide triphosphate. In some embodiments, the 2' fluoro-modified nucleotide triphosphate is selected from 2'-Fluoro-2'-deoxyadenosine-5'-Triphosphate, 2'-Fluoro-2'-deoxycytidine-5'-Triphosphate, 2'-Fluoro-2'-deoxyguanosine-5'-Triphosphate, 2'-Fluoro-2'-deoxyuridine-5'-Triphosphate, or 2'-Fluoro-thymidine-5'-Triphosphate.

In certain embodiments, the phosphorothioates enzymatically incorporated are stereo-isomerically pure R or S stereoisomers. In certain embodiments, the phosphorothioates enzymatically incorporated are a racemic mixture of the two stereoisomers.

In certain embodiments, when exonuclease resistant molecules are ligated onto the target sequence or target nucleic acid, the ligated molecules may include additional properties, including sequences, useful in further processing steps. For example, certain embodiments include sequences for priming. As another example, some embodiments include overhangs for ligations. In certain embodiments, linkers and ligands are added, such as biotin to enable purification of the target sequence or uridine bases for subsequent digestion. For example, in some embodiments, the modified nucleotide triphosphate is biotinylated. In some embodiments, the biotin can be conjugated with moiety that blocks nuclease-mediated digestion.

The term "polymerase" as used herein refers to an agent (e.g., a protein) that is capable of performing primer-dependent polynucleic acid synthesis. Examples of polymerases are well known to those of skill in the art. In certain embodiments, the polymerase can utilize single-stranded DNA, double-stranded DNA, single-stranded RNA, double-stranded RNA, and/or a DNA/RNA hybrid as a substrate. As used herein, the term DNA/RNA hybrid refers to a polynucleic acid molecule comprising a DNA molecule hybridized to an RNA molecule. In certain embodiments, the polymerase can utilize multiple substrates. For example, in certain embodiments, the polymerase can utilize single-stranded DNAs and single-stranded RNAs as a template. In certain embodiments, the polymerase does not require double-stranded DNA as substrate. In certain embodiments, the polymerase is an RNA polymerase. In other embodiments, the polymerase is a DNA polymerase. In certain embodiments, the polymerase is a reverse transcriptase, in which case the product is a cDNA comprising modified nucleotide triphosphates.

The term "phosphatase" as used herein refers to an agent (e.g., a protein) that is capable of removing the terminal phosphate from a polynucleic acid molecule. Examples of polymerases are well known to those of skill in the art, such as calf intestinal alkaline phosphatase (CIP), or shrimp alkaline phosphatase (rSAP). In some embodiments, the phosphatase can utilize single-stranded DNA, double-stranded DNA, single-stranded RNA, double-stranded RNA, and/or a DNA/RNA hybrid as a substrate. In some embodiments, the phosphatase can utilize multiple substrates. For example, in some embodiments, the phosphatase can utilize single-stranded DNAs and single-stranded RNAs as a template. In some embodiments, the phosphatase does not require double-stranded DNA as substrate.

The term "modified polynucleic acid molecule" as used herein refers to a polynucleic acid molecule comprising modified nucleotides. The abundance of modified nucleotides may vary between modified polynucleic acid molecules. For example, in some embodiments, less than 25% of the nucleotides in a modified polynucleic acid molecule are modified nucleotides. In other embodiments, at least 25%, at least 30%, at least 40%, at least 50%, at least 60%, at least 70%, at least 80%, at least 90%, or 100% of the nucleotides in a modified polynucleic acid molecule are modified nucleotides. In certain embodiments, the modified polynucleic acid molecule comprises at least one phosphorothioate linkage, N3' phosphoramidate linkage, boranophosphate internucleotide linkage, or phosphonoacetate linkage.

The term "modified polynucleic acid molecule" as used herein also refers to a dephosphorylated polynucleic acid molecule. In some embodiments, the modified polynucleic acid molecule comprises a single stranded dephosphorylated polynucleic acid molecule. In other embodiments, the modified polynucleic acid molecule comprises a double-stranded dephosphorylated polynucleic acid molecule in which one or both strands are dephosphorylated.

In some embodiments, the modified polynucleic acid molecule is single-stranded DNA (including cDNA), double-stranded DNA (including cDNA), single-stranded RNA, double-stranded RNA, or a complex of DNA and/or RNA. For example, in some embodiments, one strand of a double-stranded DNA molecule will comprise modified nucleotides, while the other strand does not. In other embodiments, both strands of a double-stranded DNA molecule will comprise modified nucleotides. In other embodiments, one strand of a double-stranded RNA molecule will comprise modified nucleotides, while the other strand does not. In other embodiments, both strands of a double-stranded RNA molecule will comprise modified nucleotides. In other embodiments, the modified polynucleic acid molecule comprises a DNA/RNA hybrid in which either the DNA or the RNA comprises modified nucleotides. In other embodiments, the modified polynucleic acid molecule comprises a DNA/RNA hybrid in which both the DNA and the RNA comprise modified nucleotides. In some embodiments, the modified polynucleic acid molecule is a combination of one or more single-stranded DNAs, double-stranded DNAs, single-stranded RNAs, double-stranded RNAs, or DNA/RNA hybrids.

As used herein, the term "resistant to nuclease-mediated cleavage" refers to a decrease in the modified polynucleic acid's susceptibility to nuclease-mediated cleavage by at least 20%, 25%, 30%, 40%, 50%, 60%, 70%, 80%, 90%, or up to 100% relative to a non-modified polynucleic acid molecule. Methods of measuring and comparing levels of nuclease-mediated cleavage are known to those skilled in the art. In some embodiments, the modified polynucleic acid molecule is resistant to all nucleases. In some embodiments, the modified polynucleic acid molecule is resistant to all exonucleases. In other embodiments, the polynucleic acid molecule is resistant to all endonucleases. In still other embodiments, the modified polynucleic acid molecule is resistant to a subset of exonucleases or endonucleases. In other embodiments, the modified polynucleic acid molecule is resistant to a single exonuclease or endonuclease.

While the concentrations of the components utilized in the embodiments disclosed herein (e.g., the modified nucleotide triphosphates, the primer(s), and the polynucleic acid molecules) may vary, the methods can utilize any effective amount of the components. As such, the contents of the reaction mixtures and the reaction incubation times may vary. "Any effective amount of the components" refers to any amount that, when combined, results in the enrichment of at least 50%, 100%, 500%, 1000%, 10,000%, 100,000%, 1,000,000% or more than 1,000,000% in the level of a polynucleic acid region of interest relative to other polynucleic acid molecules.

As used herein, the term "overhang" refers to a stretch of unpaired nucleotides at the end of a double stranded polynucleic acid molecule. The length of an overhang may vary. In some embodiments, the overhang is a short as a single nucleotide. In other embodiments, the overhang is between about 1 and 15 nucleotides in length. In other embodiments, the overhang is between about 15 and 100 nucleotides in length. In other embodiments, the overhang is greater than 100 nucleotides in length.

As used herein, the term "CRISPR/Cas complex" refers to a CRISPR/Cas protein that is bound to a small guide RNA. As used herein, the term "CRISPR/Cas protein" refers to an RNA-guided DNA endonuclease, including, but not limited to, Cas9, Cpf1, C2c1, and C2c3 and each of their orthologs and functional variants. CRISPR/Cas protein orthologs have been identified in many species and are known or recognizable to those of ordinary skill in the art. For example, Cas9 orthologs have been described in various species, including, but not limited to *Bacteroides coprophilus* (e.g., NCBI Reference Sequence: WP_008144470.1), *Campylobacter jejuni* susp. *jejuni* (e.g., GeneBank: AJP35933.1), *Campylobacter lari* (e.g., GeneBank: AJD02827.1), *Fancisella novicida* (e.g., UniProtKB/Swiss-Prot: A0Q5Y3.1), *Filifactor alocis* (e.g., NCBI Reference Sequence: WP_083799662.1), *Flavobacterium columnare* (e.g., GeneBank: AMA50561.1), *Fluviicola taffensis* (e.g., NCBI Reference Sequence: WP_013687888.1), *Gluconacetobacter diazotrophicus* (e.g., NCBI Reference Sequence: WP_041249387.1), *Lactobacillus farciminis* (e.g., NCBI Reference Sequence: WP_010018949.1), *Lactobacillus johnsonii* (e.g., GeneBank: KXN76786.1), *Legionella pneumophila* (e.g., NCBI Reference Sequence: WP_062726656.1), *Mycoplasma gallisepticum* (e.g., NCBI Reference Sequence: WP_011883478.1), *Mycoplasma mobile* (e.g., NCBI Reference Sequence: WP_041362727.1), *Neisseria cinerea* (e.g., NCBI Reference Sequence: WP_003676410.1), *Neisseria meningitidis* (e.g., GeneBank: ODP42304.1), *Nitratifractor salsuginis* (e.g., NCBI Reference Sequence: WP_083799866.1), *Parvibaculum lavamentivorans* (e.g., NCBI Reference Sequence: WP_011995013.1), *Pasteurella multocida* (e.g., GeneBank: KUM14477.1), *Sphaerochaeta globusa* (e.g., NCBI Reference Sequence: WP_013607849.1), *Streptococcus pasteurianus* (e.g., NCBI Reference Sequence: WP_061100419.1), *Streptococcus thermophilus* (e.g., GeneBank: ANJ62426.1), *Sutterella wadsworthensis* (e.g., NCBI Reference Sequence: WP_005430658.1), and *Treponema denticola* (e.g., NCBI Reference Sequence: WP_002684945.1).

In a preferred embodiment, the binding protein comprises Cas endonuclease/guide RNA complexes. Embodiments of the invention use proteins that are originally encoded by genes that are associated with clustered regularly interspaced short palindromic repeats (CRISPR) in bacterial genomes. Preferred embodiments use a CRISPR-associated (Cas) endonuclease. For such embodiments, the binding protein in a Cas endonuclease complexed with a guide RNA that targets the Cas endonuclease to a specific sequence. Any suitable Cas endonuclease or homolog thereof may be used. A Cas endonuclease may be Cas9 (e.g., spCas9), catalytically inactive Cas (dCas such as dCas9), Cpf1, C2c2, others, modified variants thereof, and similar proteins or macromolecular complexes.

In certain embodiments, the Cas endonuclease complexes (or sets of complexes if nickases are used) define the locus that includes a junction of a known mutation. The complexes protect the segment of nucleic acid that includes the boundary. One or more exonucleases may be used to digest unprotected nucleic acid. In some embodiments, the exonucleases destroy all DNA that does not include both binding/protecting sites.

The only DNA that remains includes the junction, or boundary, of the known mutation. As a result of digestion by exonuclease, unprotected nucleic acid is removed from the sample. The target nucleic acid remains in the sample, to which the Cas endonuclease may remain bound. The method further includes detecting the target nucleic acid as present after the digestion step. Any suitable detection technique may be used. For example, non-limiting detection techniques include DNA staining, spectrophotometry, sequencing, fluorescent probe hybridization, fluorescence resonance energy transfer, optical microscopy, and electron microscopy.

The Cas9/gRNA complexes may be subsequently or previously labeled using standard procedures. Single molecule analysis identifying coincidence signal of the two Cas9/gRNA complexes located on the same DNA molecule may identify the presence of the clinically informative fusion of interest. The complexes may be fluorescently labeled, e.g., with distinct fluorescent labels such that detecting involves detecting both labels together (e.g., after a dilution into fluid partitions). The complexes may be labeled with a FRET system such that they fluoresce only when bound to the same target nucleic acid.

As used herein, the term "functional variants" includes polypeptides which are about 70% identical, at least about 80% identical, at least about 90% identical, at least about 95% identical, at least about 98% identical, at least about 99% identical, at least about 99.5% identical, or at least about 99.9% identical to a protein's native amino acid sequence (i.e., wild-type amino acid sequence) and which retain functionality.

The term "functional variants" also includes polypeptides which are shorter or longer than a protein's native amino acid sequence by about 5 amino acids, by about 10 amino acids, by about 15 amino acids, by about 20 amino acids, by about 30 amino acids, by about 40 amino acids, by about 50 amino acids, by about 75 amino acids, by about 100 amino acids or more and which retain functionality.

The term "functional variants" also includes fusion proteins which retain functionality (e.g., fusion proteins that contain the binding domain of a CRISPR/Cas protein). The term "fusion protein" refers to the combination of two or more polypeptides/peptides in a single polypeptide chain. Fusion proteins typically are produced genetically through the in-frame fusing of the nucleotide sequences encoding for each of the said polypeptides/peptides. Expression of the fused coding sequence results in the generation of a single protein without any translational terminator between each of the fused polypeptides/peptides. Alternatively, fusion proteins also can be produced by chemical synthesis.

The term "retain functionality" refers to the ability of a CRISPR/Cas protein variant to bind RNA and cleave polynucleic acids at least about 5%, 10%, 20%, 25%, 30%, 40%, 50%, 60%, 70%, 75%, 80%, 90%, 100%, or more than 100% as efficiently as the respective non-variant (i.e., wild-type) CRISPR/Cas protein. Methods of measuring and comparing the efficiency of RNA binding and polynucleic acid cleavage are known to those skilled in the art.

As used herein, the term "guide RNA" refers to a polynucleic acid molecule that has a sequence that complements a guide RNA target site, which mediates binding of the CRISPR/Cas complex to the guide RNA target site, providing the specificity of the CRISPR/Cas complex. Typically, guide RNAs that exist as single RNA species comprise two domains: a "guide" domain that shares homology to a target nucleic acid (e.g., directs binding of a CRISPR/Cas complex to a target site); and a "direct repeat" domain that binds a CRISPR/Cas protein. In this way, the sequence and length of a small guide RNA may vary depending on the specific guide RNA target site and/or the specific CRISPR/Cas protein (Zetsche et al. Cell 163, 759-71 (2015)). The term "guide RNA target site" refers to sequence that a guide RNA is designed to complement.

As used herein, the term "double stranded oligonucleotide" refers to a double stranded polynucleic acid molecule that is capable of being ligated to another polynucleic acid molecule. The length of the double stranded oligonucleotide can vary. In some embodiments, the double stranded oligonucleotide is between about 5 and 10 nucleotides in length. In other embodiments, the double stranded oligonucleotide is between about 10 and 100 nucleotides in length. In other embodiments, the double stranded oligonucleotide is greater than 100 nucleotides in length.

The abundance of modified nucleotides that a double-stranded oligonucleotide comprises may vary. For example, in some embodiments, less than 25% of the nucleotides in a double-stranded oligonucleotide are modified nucleotides. In other embodiments, at least 25%, at least 30%, at least 40%, at least 50%, at least 60%, at least 70%, at least 80%, at least 90%, or 100% of the nucleotides in the double-stranded oligonucleotide are modified nucleotides.

The target nucleic acid may be detected by any means known in the art. For example and without limitation, the target nucleic acid may be detected by DNA staining, spectrophotometry, sequencing, fluorescent probe hybridization, fluorescence resonance energy transfer, optical microscopy, or electron microscopy. Methods of DNA sequencing are known in the art and described in, for example, Peterson, 2009, Generations of sequencing technologies, Genomics 93(2):105-11; Goodwin, 2016, Coming of age: ten years of next-generation sequencing technologies, Nat Rev Genet 17(6):333-51; and Morey, 2013, A glimpse into past, present, and future DNA sequencing, Mol Genet Metab 110(1-2):3-24, each incorporated by reference. Other methods of DNA detection are known in the art and described in, for example, Xu, 2014, Label-Free DNA Sequence Detection through FRET from a Fluorescent Polymer with Pyrene Excimer to SG, ACS Macro Lett 3(9):845-848, incorporated by reference.

Preferred embodiments of analysis do not require PCR amplification. Therefore, cost and sequence bias associated with PCR amplification are significantly reduced. Sample analysis can also be performed by a number of approaches, such as next generation sequencing (NGS), etc. Though many analytical platforms may require PCR amplification prior to analysis, preferred embodiments of analysis of the reaction products include single molecule analysis that avoids the requirement of amplification.

Methods of the invention may be used to detect and report clinically actionable information about a patient or a tumor in a patient. For example, the method may be used to provide a report describing the presence of the genomic alteration in a genome of a subject, such as structural alterations and/or mutations in DNA. When a genomic structural alteration is thus detected, a report may be provided to, for example, describe the alteration in a patient. The report preferably includes a description of the structural alteration in the subject (e.g., a patient). As such, the report may include a description of a plurality of structural alterations, mutations, or both in the patient's genome or tumor DNA. The report may give a description of a mutational landscape of a tumor. Knowledge of a mutational landscape of a tumor may be used to inform treatment decisions, monitor therapy, detect remissions, or combinations thereof. For example, where the report includes a description of a plurality of mutations, the report may also include an estimate of a tumor mutation burden (TMB) for a tumor. It may be found that TMB is predictive of success of immunotherapy in treating a tumor, and thus methods described herein may be used for treating a tumor.

Additionally, protecting a segment of DNA and digesting unprotected DNA provides a method for isolation or enrichment of DNA fragments, i.e., the protected segment. It may be found that the described enrichment technique is well-suited to the isolation/enrichment of arbitrarily long DNA fragments, e.g., thousands to tens of thousands of bases in length.

Long DNA fragment targeted enrichment, or negative enrichment, creates the opportunity of applying long read platforms in clinical diagnostics. Negative enrichment may be used to enrich "representative" genomic regions that can allow an investigator to identify "off rate" when performing CRISPR Cas9 experimentation, as well as enrich for genomic regions that would be used to determine TMB for immuno-oncology associated therapeutic treatments. In such applications, the negative enrichment technology is utilized to enrich large regions (>50 kb) within the genome of interest.

The method includes an enrichment step that leaves the target loci of interest intact and isolated as a segment of DNA. The methods are useful for the isolation of intact DNA fragments of any arbitrary length and may preferably be used in some embodiments to isolate (or enrich for) arbitrarily long fragments of DNA, e.g., tens, hundreds, thousands, or tens of thousands of bases in length or longer. Long, isolated, intact fragments of DNA may be analyzed by any suitable method such as simple detection (e.g., via staining with ethidium bromide) or by single-molecule sequencing. Embodiments of the invention provide kits that may be used in performing methods described herein.

In an embodiment of the invention, a kit is provided. The kit may include reagents for performing the steps of the methods according to the invention. For example, the reagents may include one or more of a primer, polymerase, modified nucleotide, Cas endonuclease, a guide RNA, and exonuclease. The kit may also include instructions or other materials such as pre-formatted report shells that receive information from the methods to provide a report (e.g., by uploading from a computer in a clinical services lab to a server to be accessed by a geneticist in a clinic to use in patient counseling). The reagents, instructions, and any other useful materials may be packaged in a suitable container. Kits of the invention may be made to order. For example, an investigator may use, e.g., an online tool to design guide RNA and reagents for the performance of methods. The guide RNAs may be synthesized using a suitable synthesis instrument. The synthesis instrument may be used to synthesize oligonucleotides such as gRNAs or single-guide RNAs (sgRNAs). Any suitable instrument or chemistry may be used to synthesize a gRNA. In some embodiments, the synthesis instrument is the MerMade 4 DNA/RNA synthesizer from Bioautomation (Irving, TX). Such an instrument can synthesize up to 12 different oligonucleotides simultaneously using 50, 200, or 1,000 nanomole prepacked columns. The synthesis instrument can prepare a large number of guide RNAs per run. These molecules (e.g., oligos) can be made using individual pre-packed columns (e.g., arrayed in groups of 96) or well-plates. The resultant reagents (e.g., primer, polymerase, modified nucleotide, guide RNA, endonuclease, exonuclease) can be packaged in a container for shipping as a kit.

Kits and methods of the invention are useful with methods disclosed in U.S. Provisional Patent Application 62/526,091, filed Jun. 28, 2017, for POLYNUCLEIC ACID MOLECULE ENRICHMENT METHODOLOGIES and U.S. Provisional Patent Application 62/519,051, filed Jun. 13, 2017, for POLYNUCLEIC ACID MOLECULE ENRICHMENT METHODOLOGIES, both incorporated by reference.

EXAMPLES

Example 1: Primer Extension-Mediated Polynucleotide Enrichment

A polynucleic acid region of interest, or target nucleic acid, may be selectively blocked from nuclease digestion by extension replication of the region of interest using modified nucleotide triphosphates. A primer is bound to a sequence flanking the region of interest, and a polymerase and modified triphosphates are used to generate a modified polynucleic acid molecule that is resistant to nuclease-mediated cleavage, such exonuclease-mediated digestion. Subsequent exposure of the polynucleic acid mixture to a nuclease, such as an exonuclease, results in digestion of the unprotected polynucleic acid molecules. Therefore, the target nucleic acid, or region of interest, is isolated (FIG. 1).

The generation of modified polynucleic acid molecules may be performed using various modified nucleotide triphosphates, primers, and polymerases. As an example, Lambda dsDNA was used as a template. First, the Lambda dsDNA was denatured according to the following composition and protocol of the denaturation reaction. 10.5 ul (roughly 5.25 µg) of Lambda dsDNA (New England Biolabs) was obtained. 203.5 µL dH2O were added to the Lambda dsDNA. 25 µL DLB buffer from the REPLI-g Single Cell Kit (Qiagen) was added. The mixture was mixed gently with a wide bore pipet tip and incubated at room temperature (RT) for 5 minutes. 36 µL Stop Solution from the FEPLI-g Single Cell Kit (Qiagen) was added. As an alternative, 26 µL of 0.1 N KOH was added in place of the DLB buffer and 36 µL of 0.2 M Tris, pH 7.5 in place of the Stop Solution.

Extension was then performed using Phi29 DNA Polymerase (New England Biolabs). The composition of the extension reaction was 39 µL of 10× phi29 buffer (New England Biolabs); 19.5 µL daNTP mix; 5 µL 100 µM primer (10 µL total if two primers were used); 276 µt denatured Lambda DNA; 45.5 µL dH2O (40.5 µL dH2O if two primers were used); and 5 μL phi29 DNA Polymerase (New England Biolabs). The composition of the daNTP mix was 1.5 μt dATP (100 mM stock, New England Biolabs); 1.5 μL dCTP (100 mM stock, New England Biolabs); 1.5 μL dTTP (100 mM stock, New England Biolabs); and either 13.5 μL of dH2O and 1.5 μL dGTP (100 mM stock, New England Biolabs) or 15 μL S-dGaS-TP (10 mM stock, Axxora).

Figure 2:
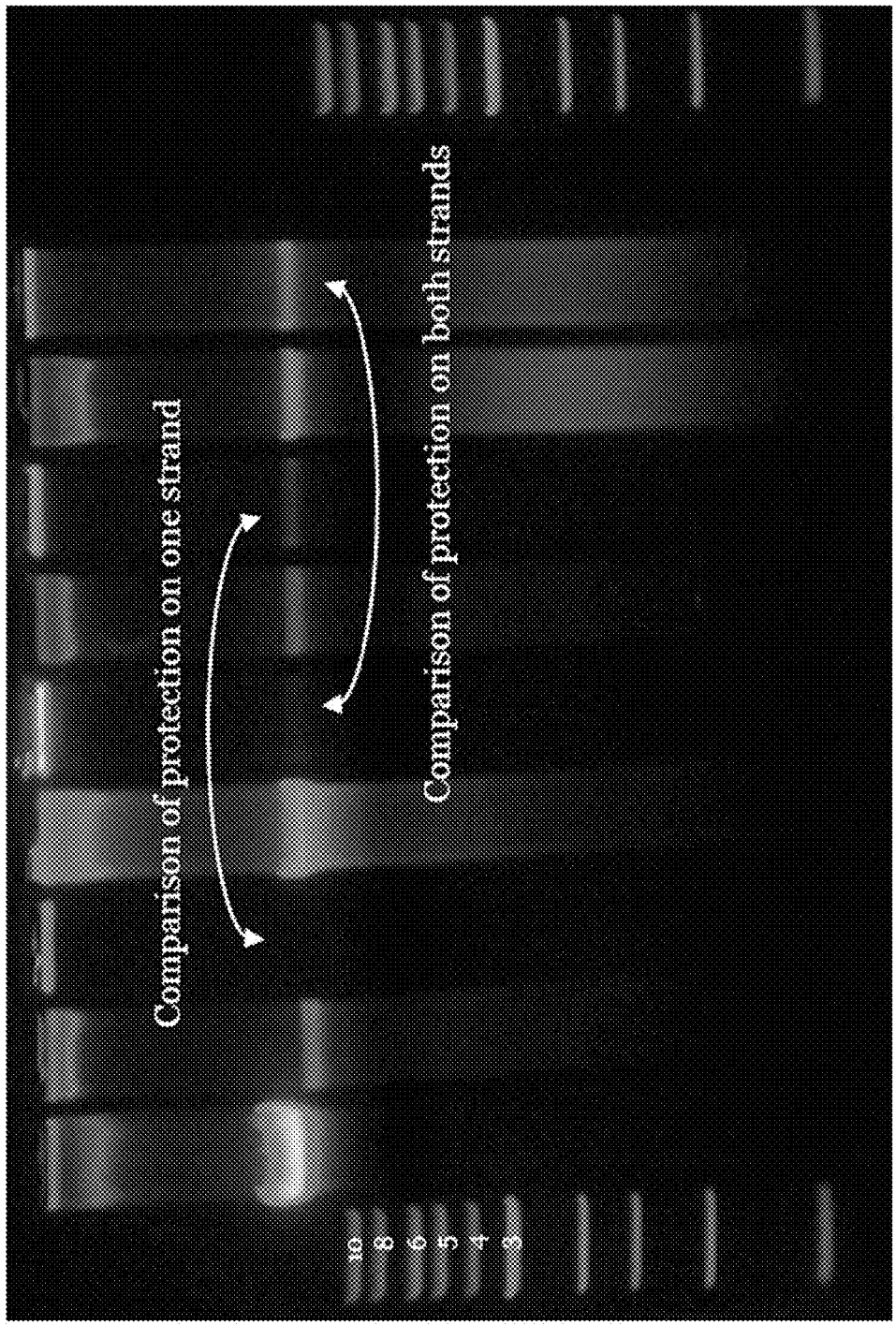
FIG. 2 shows protection of Lambda DNA via primer extension. Extension of Lambda DNA template was performed using a polymerase, one primer (Primer 1, generating PEx-1) or two primers (Primers 1 and 8, generating PEx-2), and unmodified nucleotides or modified nucleotides (GaS). Incorporation of modified nucleotides protects the extended Lambda DNA from nuclease-mediated digestion (exo).
Figure 3:
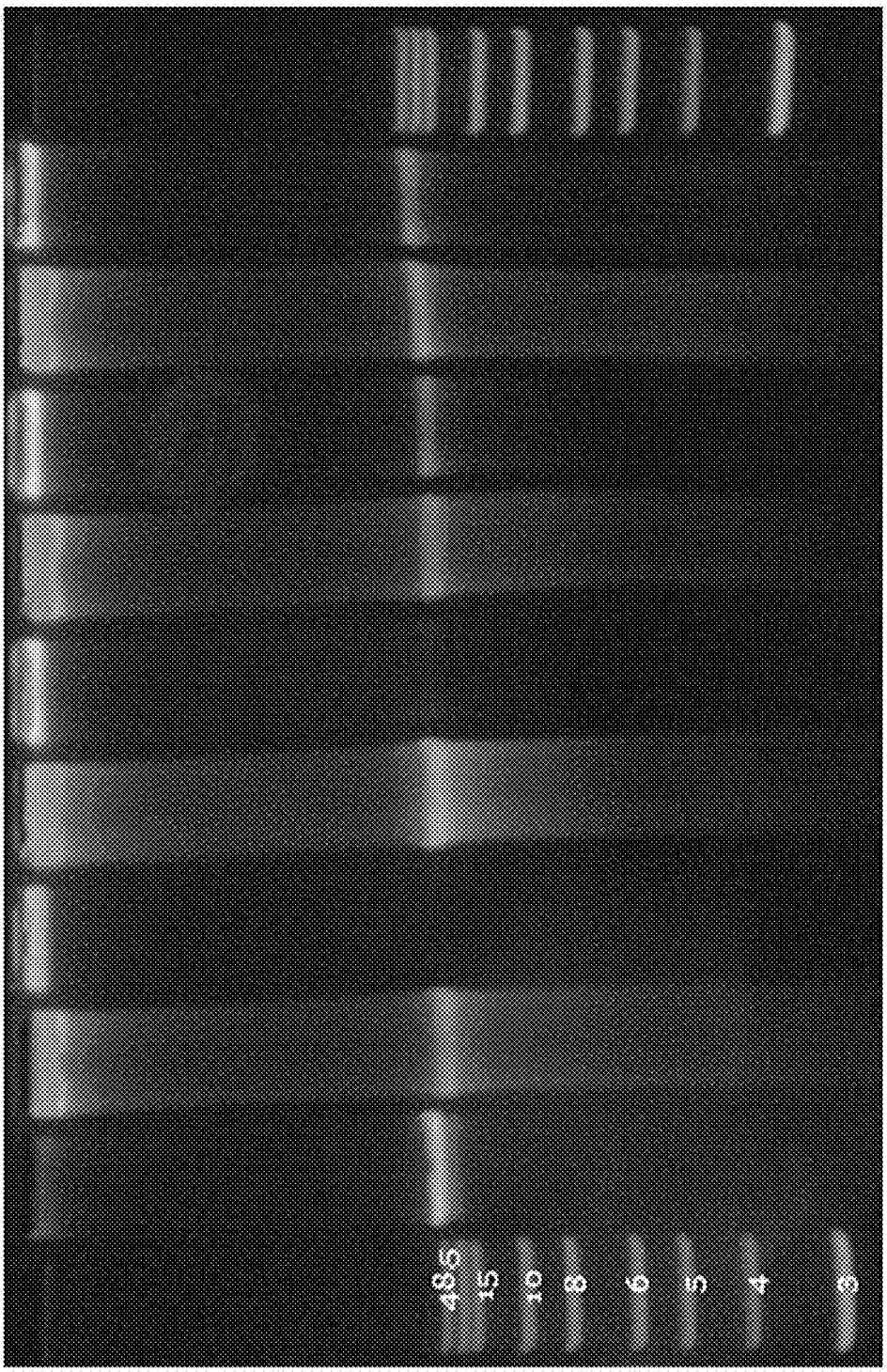
FIG. 3 shows protection of Lambda DNA via primer extension. Extension of Lambda DNA template was performed using a polymerase, one primer (Primer 3, generating PEx-1) or two primers (Primers 3 and 6, generating PEx-2), and unmodified nucleotides or modified nucleotides (GaS). Incorporation of modified nucleotides protects the extended Lambda DNA from nuclease-mediated digestion (exo).
Figure 4:
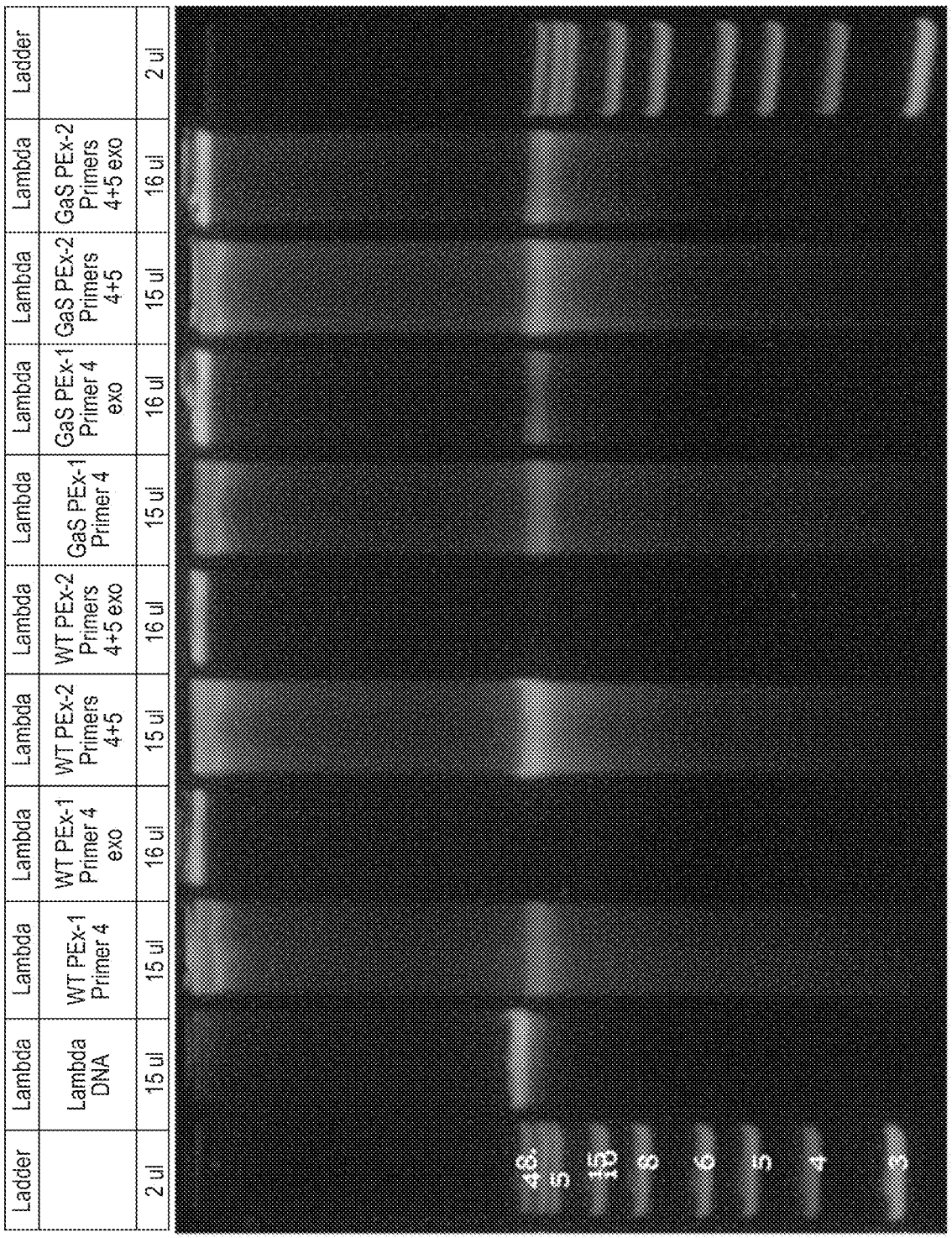
FIG. 4 shows protection of Lambda DNA via primer extension. Extension of Lambda DNA template was performed using a polymerase, one primer (Primer 4, generating PEx-1) or two primers (Primers 4 and 5, generating PEx-2), and unmodified nucleotides or modified nucleotides (GaS). Incorporation of modified nucleotides protects the extended Lambda DNA from nuclease-mediated digestion (exo).

The extended samples were then exposed to Exonuclease III and resolved on a gel (FIG. 2-4). Incorporation of modified nucleotides protected the extended Lambda DNA from nuclease-mediated digestion. Moreover, results showed that protection using two primers (i.e., incorporation of modified nucleotides into both strands) was more effective than protection using one primer (i.e., incorporation of modified nucleotides into one strand only).

Example 2: End Protection-Mediated Polynucleotide Enrichment

Enrichment of a polynucleotide region of interest may be facilitated by filling 3' overhang ends of DNA using modified nucleotides. The ends of Lambda DNA have 12-base 5' overhangs. As such, the 3' strand of the Lambda DNA may be filled in with modified bases.

Figure 5:
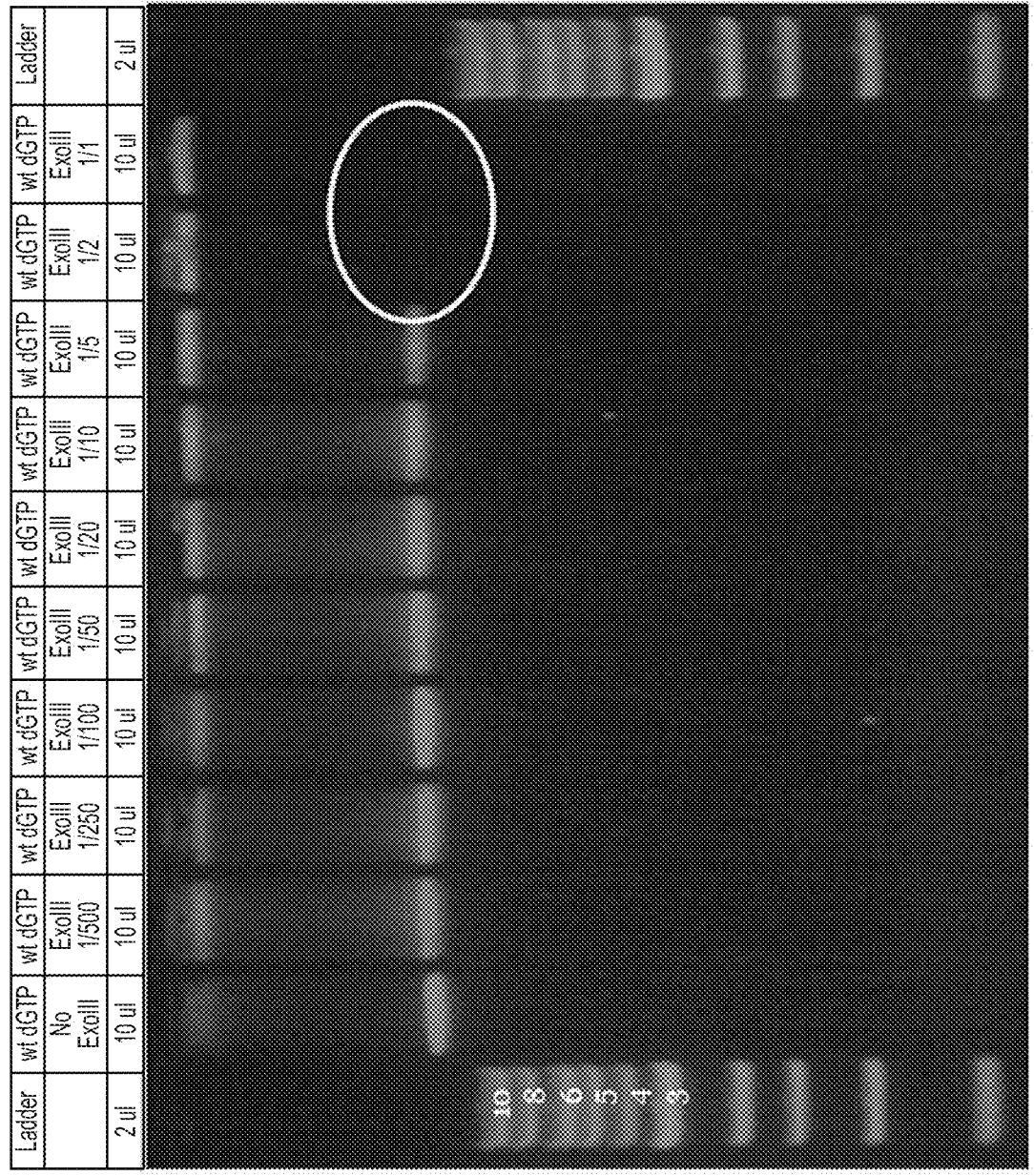
FIG. 5 shows End protection of Lambda DNA via extension. The ends of Lambda DNA have 12-base 5' overhangs; thus, the 3' strand can be filled in using a polymerase and nucleotide triphosphates. Incorporating modified nucleotides bases in the 3' strands of the Lambda DNA protects it from nuclease-mediated digestion.
Figure 6:
FIG. 6 shows end protection of Lambda DNA via extension. The ends of Lambda DNA have 12-base 5' overhangs; thus, the 3' strand can be filled in using a polymerase and modified nucleotide triphosphates. Incorporating modified nucleotides bases in the 3' strands of the Lambda DNA protects it from nuclease-mediated digestion.

To demonstrate the utility of this approach, an extension reaction with Klenow enzyme on stock Lambda DNA template was performed. dATP, dTTP, dCTP, and either dGTP or S-dGaS-TP were used as modified bases. The extended samples were then exposed to Exonuclease III and resolved on a gel (FIGS. 5 and 6). Results showed that incorporation of modified nucleotides protected the extended Lambda DNA from nuclease-mediated digestion.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present invention are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present invention.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B," when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B," the disclosure also contemplates the alternative embodiments "a composition consisting of A and B" and "a composition consisting essentially of A and B."

What is claimed is:

1. A method for isolating a target nucleic acid, the method comprising:
    hybridizing at least one primer to a target nucleic acid in a sample comprising non-target nucleic acids;
    extending the primer using a polymerase and modified nucleotides that are resistant to nuclease degradation to create a modified polynucleotide that protects the target nucleic acid from nuclease degradation; and
    exposing the sample to an exonuclease to digest the non-target nucleic acids, thereby isolating the target nucleic acid.

2. The method of claim 1, wherein the modified nucleotides comprise modified nucleotide triphosphates.

3. The method of claim 2, wherein the modified nucleotide triphosphates comprise alpha-phosphorothioate nucleotide triphosphates, morpholino triphosphates, peptide nucleic acids, peptide nucleic acid analogs, or sugar modified nucleotide triphosphates.

4. The method of claim 3, wherein the modified nucleotide triphosphates are selected from the group consisting of 2'-Deoxycytidine-5'-O-(1-Thiotriphosphate), 2'-O-methyl modified nucleotide triphosphate, 2'-fluoro modified nucleotide, 2'-O-Methyladenosine-5'-Triphosphate, 2'-O-Methylcytidine-5'-Triphosphate, 2'-O-Methylguanosine-5'-Triphosphate, 2'-0-Methyluridine-5'-Triphosphate, 2'-O-Methylinosine-5'-Triphosphate, 2'-O-Methyl-2-aminoadenosine-5'-Triphosphate, 2'-O-Methylpseudouridine-5'-Triphosphate, 2'-O-Methyl-5-methyluridine-5'-Triphosphate, 2'-O-Methyl-N6-Methyladenosine-5'-Triphosphate, 2'-Fluoro-2'-deoxyadenosine-5'-Triphosphate, 2'-Fluoro-2'-deoxycytidine-5'-Triphosphate, 2'-Fluoro-2'-deoxyguanosine-5'-Triphosphate, 2'-Fluoro-2'-deoxyuridine-5'-Triphosphate, and 2'-Fluoro-thymidine-5'-Triphosphate.

5. The method of claim 1, wherein natural nucleotides are used in combination with modified nucleotides.

6. The method of claim 1, wherein two primers are used for hybridization.

7. The method of claim 6, further comprising amplification of the modified polynucleotide.

8. The method of claim 2, further comprising dephosphorylating the target nucleic acid using a phosphatase.

9. The method of claim 1, further comprising detecting the target nucleic acid.

10. The method of claim 1, wherein the target comprises circulating tumor DNA.

11. The method of claim 10, wherein the sample is a blood sample, serum sample, or plasma sample.

12. A method for isolating a target nucleic acid, the method comprising:
    hybridizing at least one primer to a first end of a target nucleic acid in a sample comprising non-target nucleic acids;
    extending the primer using a polymerase and modified nucleotides that are resistant to nuclease degradation to create a modified polynucleotide that protects the target nucleic acid from nuclease digestion;
    binding at least one protein to a second end of the target nucleic acid in a sequence-specific manner to create protected target nucleic acid resistant to nuclease degradation; and
    exposing the sample to an exonuclease to digest the non-target nucleic acids, thereby isolating the protected target nucleic acid.

13. The method of claim 12, wherein the modified nucleotides comprise modified nucleotide triphosphates.

14. The method of claim 12, wherein natural nucleotides are used in combination with modified nucleotides.

15. The method of claim 13, wherein the modified nucleotide triphosphates comprise alpha-phosphorothioate nucleotide triphosphates, morpholino triphosphates, peptide nucleic acids, peptide nucleic acid analogs, or sugar modified nucleotide triphosphates.

16. The method of claim 15, wherein the modified nucleotide triphosphates are selected from the group consisting of 2'-Deoxycytidine-5'-O-(1-Thiotriphosphate), 2'-O-methyl modified nucleotide triphosphate, 2'-fluoro modified nucleotide, 2'-O-Methyladenosine-5'-Triphosphate, 2'-O-Methylcytidine-5'-Triphosphate, 2'-O-Methylguanosine-5'-Triphosphate, 2'-0-Methyluridine-5'-Triphosphate, 2'-O-Methylinosine-5'-Triphosphate, 2'-O-Methyl-2-aminoadenosine-5'-Triphosphate, 2'-O-Methylpseudouridine-5'-Triphosphate, 2'-O-Methyl-5-methyluridine-5'-Triphosphate, 2'-O-Methyl-N6-Methyladenosine-5'-Triphosphate, 2'-Fluoro-2'-deoxyadenosine-5'-Triphosphate, 2'-Fluoro-2'-deoxycytidine-5'-Triphosphate, 2'-Fluoro-2'-deoxyguanosine-5'-Triphosphate, 2'-Fluoro-2'-deoxyuridine-5'-Triphosphate, and 2'-Fluoro-thymidine-5'-Triphosphate.

17. The method of claim 13, wherein the at least one protein comprises a Cas endonuclease complexed with a guide RNA that targets the Cas endonuclease to a region of the target nucleic acid.

18. The method of claim 17, wherein the Cas endonuclease is catalytically inactive.

19. The method of claim 13, further comprising detecting the target nucleic acid.

20. The method of claim 19, wherein the detecting step comprises using hybridization, spectrophotometry, sequencing, electrophoresis, amplification, fluorescence detection, chromatography, DNA staining, or microscopy.

21. The method of claim 13, wherein the sample is a blood sample, serum sample, plasma sample, urine sample, saliva sample, semen sample, feces sample, phlegm sample, or liquid biopsy.

* * * * *